(12) United States Patent
Timm et al.

(10) Patent No.: US 7,615,068 B2
(45) Date of Patent: Nov. 10, 2009

(54) MOUNTING MECHANISMS FOR PEDICLE SCREWS AND RELATED ASSEMBLIES

(75) Inventors: Jens Peter Timm, West Haven, CT (US); Bryan Hildebrand, Orange, CT (US); Ronald Callahan, Naugatuck, CT (US); Ernest Corrao, Bethel, CT (US); Stephen Maguire, Shelton, CT (US); Carmen Walters, Hamden, CT (US)

(73) Assignee: Applied Spine Technologies, Inc., Rocky Hill, CT (US)

( * ) Notice: Subject to any disclaimer, the term of this patent is extended or adjusted under 35 U.S.C. 154(b) by 0 days.

(21) Appl. No.: 11/027,245

(22) Filed: Dec. 31, 2004

(65) Prior Publication Data
US 2005/0177166 A1   Aug. 11, 2005

Related U.S. Application Data

(60) Provisional application No. 60/581,716, filed on Jun. 23, 2004.

(51) Int. Cl.
*A61B 17/70* (2006.01)
*A61B 17/58* (2006.01)

(52) U.S. Cl. .......................... 606/266; 606/305
(58) Field of Classification Search .............. 606/61, 606/72–73
See application file for complete search history.

(56) References Cited

U.S. PATENT DOCUMENTS

| | | | |
|---|---|---|---|
| 4,504,165 A | 3/1985 | Moeremans | |
| 4,565,345 A | 1/1986 | Templeman | |
| 5,047,029 A * | 9/1991 | Aebi et al. | ...................... 606/61 |
| 5,092,867 A | 3/1992 | Harms et al. | |
| 5,207,678 A | 5/1993 | Harms et al. | |
| 5,375,823 A | 12/1994 | Navas | |
| 5,474,551 A * | 12/1995 | Finn et al. | ...................... 606/61 |
| 5,480,401 A | 1/1996 | Navas | |
| 5,501,684 A | 3/1996 | Schlapfer et al. | |
| 5,540,688 A | 7/1996 | Navas | |

(Continued)

FOREIGN PATENT DOCUMENTS

CA    2213058    2/1998

(Continued)

OTHER PUBLICATIONS

PCT International Search Report dated Feb. 22, 2006.

*Primary Examiner*—Eduardo C Robert
*Assistant Examiner*—Mary Hoffman
(74) *Attorney, Agent, or Firm*—McCarter & English, LLP

(57) ABSTRACT

A pedicle screw is provided that includes an upwardly extending collet. The collet may include downwardly extending slots that define deflectable segments therebetween. When a spherical element or other structure, e.g., a non-dynamic stabilizing element, is positioned around the collet, introduction of a set screw causes outward deflection of the upstanding segments into engagement with the spherical element. A snap ring may be interposed between the collet and the spherical element to facilitate positioning therebetween. In an alternative embodiment, a non-slotted collet is employed. In such embodiment, the collet and the spherical element may be threadingly engaged and may include a snap ring therebetween. The pedicle screw subassemblies may be incorporated into a spinal stabilization system which may include a dynamic stabilizing member to provide clinically efficacious results.

17 Claims, 28 Drawing Sheets

U.S. PATENT DOCUMENTS

| | | | |
|---|---|---|---|
| 5,562,357 A | 10/1996 | Sandell | |
| 5,562,737 A | 10/1996 | Graf | |
| 5,672,175 A | 9/1997 | Martin | |
| 5,681,311 A | 10/1997 | Foley et al. | |
| 5,713,900 A | 2/1998 | Benzel et al. | |
| 5,735,853 A | 4/1998 | Olerud | |
| 5,746,548 A | 5/1998 | Crandall | |
| 5,882,350 A * | 3/1999 | Ralph et al. | 606/61 |
| 5,902,303 A | 5/1999 | Eckhof et al. | |
| 5,938,663 A * | 8/1999 | Petreto | 606/61 |
| 5,961,516 A | 10/1999 | Graf | |
| 6,030,389 A | 2/2000 | Wagner et al. | |
| 6,090,111 A | 7/2000 | Nichols | |
| 6,106,526 A | 8/2000 | Harms et al. | |
| 6,146,383 A | 11/2000 | Studer et al. | |
| 6,162,234 A * | 12/2000 | Freedland et al. | 606/151 |
| 6,187,005 B1 | 2/2001 | Brace et al. | |
| 6,235,033 B1 | 5/2001 | Brace et al. | |
| 6,296,642 B1 | 10/2001 | Morrison et al. | |
| 6,302,888 B1 | 10/2001 | Mellinger et al. | |
| 6,309,390 B1 | 10/2001 | Le Couedic et al. | |
| 6,328,739 B1 * | 12/2001 | Liu et al. | 606/61 |
| 6,343,888 B1 | 2/2002 | Hühn et al. | |
| 6,371,957 B1 | 4/2002 | Amrein et al. | |
| 6,440,132 B1 * | 8/2002 | Jackson | 606/61 |
| 6,454,769 B2 | 9/2002 | Wagner et al. | |
| 6,488,681 B2 | 12/2002 | Martin et al. | |
| 6,508,818 B2 | 1/2003 | Steiner et al. | |
| 6,520,682 B2 | 2/2003 | Kletzli et al. | |
| 6,554,831 B1 | 4/2003 | Rivard et al. | |
| 6,554,834 B1 | 4/2003 | Crozet et al. | |
| 6,575,975 B2 | 6/2003 | Brace et al. | |
| 6,623,485 B2 | 9/2003 | Doubler et al. | |
| 6,626,904 B1 | 9/2003 | Jammet et al. | |
| 6,641,583 B2 | 11/2003 | Shluzas et al. | |
| 6,709,434 B1 | 3/2004 | Gournay et al. | |
| 6,716,214 B1 | 4/2004 | Jackson | |
| 6,730,089 B2 | 5/2004 | Jackson | |
| 6,733,502 B2 | 5/2004 | Altarac et al. | |
| 6,755,830 B2 | 6/2004 | Minfelde et al. | |
| 6,835,196 B2 | 12/2004 | Biedermann et al. | |
| 6,866,664 B2 * | 3/2005 | Schär et al. | 606/61 |
| 6,945,972 B2 * | 9/2005 | Frigg et al. | 606/61 |
| 7,144,396 B2 * | 12/2006 | Shluzas | 606/266 |
| 2002/0095154 A1 | 7/2002 | Atkinson et al. | |
| 2002/0143341 A1 | 10/2002 | Biedermann et al. | |
| 2003/0004512 A1 * | 1/2003 | Farris et al. | 606/61 |
| 2003/0045878 A1 | 3/2003 | Petit et al. | |
| 2003/0125741 A1 * | 7/2003 | Biedermann et al. | 606/61 |
| 2003/0163133 A1 | 8/2003 | Altarac et al. | |
| 2003/0171749 A1 | 9/2003 | Le Couedic et al. | |
| 2004/0030337 A1 | 2/2004 | Alleyne et al. | |
| 2004/0039386 A1 | 2/2004 | Kumar et al. | |
| 2004/0049189 A1 | 3/2004 | Le Couedic et al. | |
| 2004/0049190 A1 | 3/2004 | Biedermann et al. | |
| 2004/0082956 A1 | 4/2004 | Baldwin et al. | |
| 2004/0092930 A1 | 5/2004 | Petit et al. | |
| 2004/0092938 A1 | 5/2004 | Carli | |
| 2004/0097933 A1 | 5/2004 | Lourdel et al. | |
| 2004/0147928 A1 | 7/2004 | Landry et al. | |
| 2004/0167523 A1 | 8/2004 | Jackson | |
| 2004/0181223 A1 | 9/2004 | Ritland | |
| 2004/0230192 A1 | 11/2004 | Graf | |
| 2004/0236330 A1 | 11/2004 | Purcell et al. | |
| 2004/0243126 A1 | 12/2004 | Carbone et al. | |
| 2004/0254574 A1 | 12/2004 | Morrison et al. | 606/61 |
| 2005/0070899 A1 | 3/2005 | Doubler et al. | 606/61 |
| 2005/0070901 A1 | 3/2005 | David | 606/61 |
| 2006/0149234 A1 | 7/2006 | De Coninck | 606/61 |
| 2006/0247624 A1 | 11/2006 | Banouskou et al. | 606/61 |
| 2006/0282074 A1 | 12/2006 | Renaud et al. | 606/61 |
| 2007/0016200 A1 | 1/2007 | Jackson | 606/61 |

FOREIGN PATENT DOCUMENTS

| | | |
|---|---|---|
| EP | 0516567 | 12/1992 |
| EP | 0821917 | 2/1998 |
| FR | 2676911 | 12/1992 |
| FR | 2751864 | 2/1998 |
| FR | 2799949 | 4/2001 |
| FR | 2801782 | 6/2001 |
| FR | 2803188 | 7/2001 |
| FR | 2809304 | 11/2001 |
| GB | 2382304 | 5/2003 |
| JP | 10-71157 | 3/1998 |
| WO | 01/39678 | 6/2001 |
| WO | 01/45576 | 6/2001 |
| WO | 01/49192 | 7/2001 |
| WO | 2004/052218 | 6/2004 |

* cited by examiner

DSS in Tension

DSS in Tension

MOUNTING MECHANISMS FOR PEDICLE SCREWS AND RELATED ASSEMBLIES

CROSS REFERENCE TO RELATED APPLICATIONS

The present application claims the benefit of a provisional application entitled "Dynamic Spine Stabilization," filed on Jun. 23, 2004 and assigned Ser. No. 60/581,716. In addition, the foregoing provisional patent applications is incorporated in its entirety herein by reference to the extent not inconsistent herewith.

BACKGROUND OF THE INVENTION

1. Technical Field

The present disclosure relates to advantageous methods and apparatus for spinal stabilization. More particularly, the present disclosure relates to methods and apparatus for providing dynamic stabilization to the spine so as to provide clinically efficacious results.

2. Background Art

Low back pain is one of the most expensive diseases afflicting industrialized societies. With the exception of the common cold, it accounts for more doctor visits than any other ailment. The spectrum of low back pain is wide, ranging from periods of intense disabling pain which resolve to varying degrees of chronic pain. The conservative treatments available for lower back pain include: cold packs, physical therapy, narcotics, steroids and chiropractic maneuvers. Once a patient has exhausted all conservative therapy, the surgical options generally range from micro discectomy, a relatively minor procedure to relieve pressure on the nerve root and spinal cord, to fusion, which takes away spinal motion at the level of pain.

Each year, over 200,000 patients undergo lumbar fusion surgery in the United States. While fusion is effective about seventy percent of the time, there are consequences even to these successful procedures, including a reduced range of motion and an increased load transfer to adjacent levels of the spine, which may accelerate degeneration at those levels. Further, a significant number of back-pain patients, estimated to exceed seven million in the U.S., simply endure chronic low-back pain, rather than risk procedures that may not be appropriate or effective in alleviating their symptoms.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, e.g., the Dynesys stabilization system (Zimmer, Inc.; Warsaw, Ind.) and the Graf Ligament. A major goal of this concept is the stabilization of the spine to prevent pain while preserving near normal spinal function. The primary difference in the two types of motion preservation devices is that replacement devices are utilized with the goal of replacing degenerated anatomical structures which facilitate motion while dynamic internal stabilization devices are utilized with the goal of stabilizing and controlling abnormal spinal motion.

Over ten years ago a hypothesis of low back pain was presented in which the spinal system was conceptualized as consisting of the spinal column (vertebrae, discs and ligaments), the muscles surrounding the spinal column, and a neuromuscular control unit which helps stabilize the spine during various activities of daily living. Panjabi MM. "The stabilizing system of the spine. Part I. Function, dysfunction, adaptation, and enhancement." *J Spinal Disord* 5 (4): 383-389, 1992a. A corollary of this hypothesis was that strong spinal muscles are needed when a spine is injured or degenerated. This was especially true while standing in neutral posture. Panjabi MM. "The stabilizing system of the spine. Part II. Neutral zone and instability hypothesis." *J Spinal Disord* 5 (4): 390-397, 1992b. In other words, a low-back patient needs to have sufficient well-coordinated muscle forces, strengthening and training the muscles where necessary, so they provide maximum protection while standing in neutral posture.

Dynamic stabilization (non-fusion) devices need certain functionality in order to assist the compromised (injured or degenerated with diminished mechanical integrity) spine of a back patient. Specifically, the devices must provide mechanical assistance to the compromised spine, especially in the neutral zone where it is needed most. The "neutral zone" refers to a region of low spinal stiffness or the toe-region of the Moment-Rotation curve of the spinal segment (see FIG. 1). Panjabi MM, Goel V K, Takata K. 1981 Volvo Award in Biomechanics. "Physiological Strains in Lumbar Spinal Ligaments, an in vitro Biomechanical Study." *Spine* 7 (3): 192-203, 1982. The neutral zone is commonly defined as the central part of the range of motion around the neutral posture where the soft tissues of the spine and the facet joints provide least resistance to spinal motion.

This concept may be visualized with reference to load-displacement or moment-rotation curves for an intact spine and an injured spine, as shown in FIG. 1. The curves are non-linear; that is, the spine mechanical properties change with the amount of angulations and/or rotation. If the curves on the positive and negative sides are understood to represent spinal behavior in flexion and extension, respectively, then the slope of the curve at each point represents spinal stiffness. As seen in FIG. 1, the neutral zone is the low stiffness region of the range of motion.

Experiments have shown that after an injury to the spinal column and/or degeneration of the spine, neutral zones, as well as ranges of motion, increase (see FIG. 1). However, the neutral zone increases to a greater extent than does the range of motion, when described as a percentage of the corresponding intact values. This implies that the neutral zone may be a better measure of spinal injury and instability than the range of motion. Clinical studies have also found that range of motion does not correlate well with low back pain. Therefore, an unstable spine needs to be stabilized, especially in the neutral zone.

With the foregoing in mind, those skilled in the art will understand that a need exists for spinal stabilization devices, systems and/or methods that overcome the shortcomings of prior art devices, systems and methods. The present invention provides devices, systems and methods for enhanced and efficacious spinal stabilization. More particularly, the present disclosure provides advantageous dynamic internal stabilization devices, systems and methods that are flexible so as to move with the spine, thus allowing the disc, the facet joints, and the ligaments normal (or improved) physiological motion and loads necessary for maintaining their nutritional well-being. The devices, systems and methods of the present disclosure also advantageously accommodate different physical characteristics of individual patients and anatomies to achieve a desired and/or improved posture for each individual patient.

SUMMARY OF THE PRESENT DISCLOSURE

According to the present disclosure, advantageous devices, systems and methods for spinal stabilization are provided. According to preferred embodiments of the present disclosure, the disclosed devices, systems and methods provide dynamic stabilization to the spine so as to provide clinically efficacious results. In addition, the disclosed devices, systems and methods offer clinical advantages, including ease of installation, versatility/flexibility in application, and superior clinical results for individuals encountering lower back pain and other spine-related difficulties.

According to exemplary implementations of the present disclosure, devices, systems and methods are provided that encompass one or more pedicle screws for attachment to spinal structures. The pedicle screw(s) of the present disclosure are typically employed as part of a spine stabilization system that includes one or more of the following advantageous structural and/or functional attributes:

- A dynamic junction between at least one pedicle screw and at least one elongated member (or multiple elongated members), e.g., rod(s), that engage and/or otherwise cooperate with the pedicle screw;
- Advantageous assembly mechanisms that facilitate assembly/installation of a ball/sphere or other accessory component relative to the pedicle screw and provide advantageous functional attributes as part of a spinal stabilization system. Exemplary mechanisms include advantageous collet-based mechanisms, cooperatively threaded mechanisms, mechanisms that apply bearing forces against a ball/sphere or other accessory component, and/or mechanisms that include a snap ring or analogous structure;
- Advantageous multi-level dynamic spine stabilization systems/implementations, including multi-level systems that permit one or more adjustments to be made (e.g., in situ and/or prior to clinical installation), e.g., adjustments as to the magnitude and/or displacement-response characteristics of the forces applied by the stabilization system; according to exemplary multi-level implementations of the present disclosure, different stabilization modalities may be employed at individual stabilization levels, e.g., by mixing of dynamic and non-dynamic stabilizing structures between adjacent pedicle screws at different stabilization levels;
- Advantageous installation accessories (e.g., cone structures) for facilitating placement/installation of spine stabilization system components, such accessories being particularly adapted for use with conventional guidewire(s) to facilitate alignment/positioning of system components relative to the pedicle screw;
- Dynamic stabilization systems and/or other surgical implants that include a cover and/or sheath structure that provides advantageous protection to inner force-imparting component(s), e.g., one or more springs, while exhibiting clinically acceptable interaction with surrounding anatomical fluids and/or structures, e.g., a cover and/or sheath structure that is fabricated (in whole or in part) from ePTFE, UHMWPE and/or alternative polymeric materials such as polycarbonate-polyurethane copolymers and/or blends;
- Advantageous dynamic spine stabilization connection systems that facilitate substantially rigid attachment of an elongated member (e.g., a rod) relative to the pedicle screw while simultaneously facilitating movement relative to adjacent structures (e.g., an adjacent pedicle screw) to permit easy and efficacious intra-operative system placement;
- An advantageous "pre-load" arrangement for a securing structure (e.g., a set screw) that may be used in situ to mount a ball joint or other accessory component relative to the pedicle screw, thereby minimizing the potential for clinical difficulties associated with location and/or alignment of such securing structure(s).

As noted above, advantageous spine stabilization devices, systems and methods may incorporate one or more of the foregoing structural and/or functional attributes. Thus, it is contemplated that a system, device and/or method may utilize only one of the advantageous structures/functions set forth above, a plurality of the advantageous structures/functions described herein, or all of the foregoing structures/functions, without departing from the spirit or scope of the present disclosure. Stated differently, each of the structures and functions described herein is believed to offer benefits, e.g., clinical advantages to clinicians and/or patients, whether used alone or in combination with others of the disclosed structures/functions.

Generally, the structures/functions of the threaded shaft portions of the pedicle screws disclosed herein are of conventional design. Thus, installation of the pedicle screws is generally undertaken by a clinician in a conventional manner. Selection and placement of the pedicle screws is generally based on conventional criteria, as are known to persons skilled in the art. However, unlike conventional pedicle-screw based systems, the devices, systems, and methods of the present disclosure offer advantageous clinical results, e.g., based on ease and flexibility of rod/elongated member placement, dynamic attributes of the rod/elongated member in situ relative to the pedicle screws, and/or dynamic force delivery in response to spinal displacement stimulus.

Additional advantageous features and functions associated with the devices, systems and methods of the present disclosure will be apparent to persons skilled in the art from the detailed description which follows, particularly when read in conjunction with the figures appended hereto. Such additional features and functions, including the structural and mechanistic characteristics associated therewith, are expressly encompassed within the scope of the present invention.

BRIEF DESCRIPTION OF THE DRAWINGS

To assist those of ordinary skill in the art in making and using the disclosed devices, systems and methods for spinal stabilization and other applications, reference is made to the appended figures wherein.

DESCRIPTION OF EXEMPLARY EMBODIMENTS

The present disclosure provides advantageous devices, systems and methods for spinal stabilization and/or alternative surgical implant applications. More particularly, the present disclosure provides devices, systems and methods that deliver dynamic stabilization to the spine so as to provide clinically efficacious results. The exemplary embodiments disclosed herein are illustrative of the advantageous spine stabilization systems and surgical implants of the present disclosure, and methods/techniques for implementation thereof. It should be understood, however, that the disclosed embodiments are merely exemplary of the present invention, which may be embodied in various forms. Therefore, the details disclosed herein with reference to exemplary dynamic spinal stabilization systems and associated methods/techniques are not to be interpreted as limiting, but merely as the basis for teaching one skilled in the art how to make and/or use the advantageous dynamic spinal stabilization systems and alternative surgical implants of the present disclosure.

With reference to FIGS. 2, 3a-e and 4, an exemplary method and apparatus for spinal stabilization are disclosed. Although the description which follows is primarily directed to spinal stabilization, it is expressly contemplated that the disclosed methods and apparatus may be advantageously employed in alternative surgical applications, e.g., any long bone application. Thus, throughout the detailed disclosure which follows, it is to be understood that references and teachings with respect to spinal stabilization are merely illustrative and that the disclosed systems, devices and methods find application in a multitude of a surgical/anatomical settings, including specifically long bone applications involving the femur, tibia, fibula, ulna, and/or humerus.

In accordance with an exemplary embodiment of the present disclosure, the spinal stabilization method is achieved by securing an internal dynamic spine stabilizing member 10 between adjacent vertebrae 12, 14, thereby providing mechanical assistance in the form of elastic resistance to the region of the spine to which the dynamic spine stabilizing member 10 is attached. The elastic resistance is applied as a function of displacement such that greater stiffness, i.e., greater incremental resistance, is provided while the spine is in its neutral zone and lesser mechanical stiffness, i.e., lesser incremental resistance, is provided while the spine bends beyond its neutral zone. Although the term elastic resistance is generally used throughout the body of the present specification, other forms of resistance may be employed without departing from the spirit of the present invention.

Figure 2:
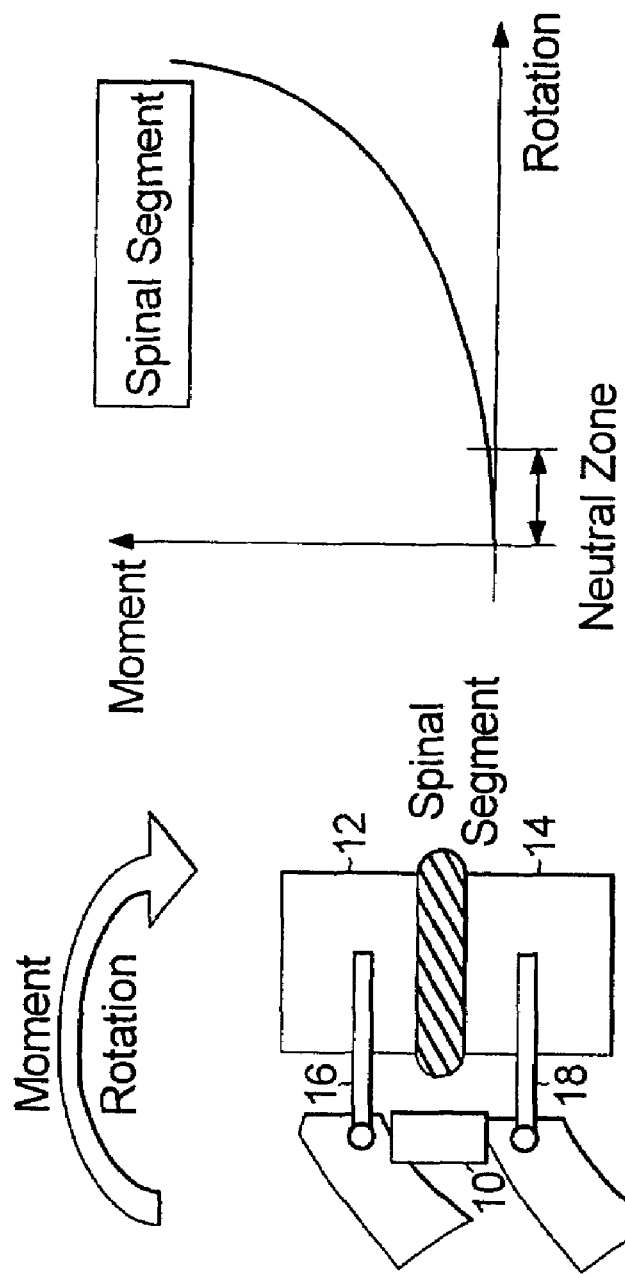
FIG. 2 is a schematic representation of a spinal segment in conjunction with a Moment-Rotation curve for a spinal segment, showing relatively low spinal stiffness within the neutral zone.

As those skilled in the art will certainly appreciate, and as mentioned above, the "neutral zone" is understood to refer to a region of low spinal stiffness or the toe-region of the Moment-Rotation curve of the spinal segment (see FIG. 2). That is, the neutral zone may be considered to refer to a region of laxity around the neutral resting position of a spinal segment where there is minimal resistance to inter-vertebral motion. The range of the neutral zone is considered to be of major significance in determining spinal stability. Panjabi, MM. "The stabilizing system of the spine. Part II. Neutral zone and instability hypothesis." *J Spinal Disorders* 1992; 5(4): 390-397.

In fact, Dr. Panjabi (a presently named inventor) has previously described the load displacement curve associated with spinal stability through the use of a "ball in a bowl" analogy. According to this analogy, the shape of the bowl indicates spinal stability. A deeper bowl represents a more stable spine, while a more shallow bowl represents a less stable spine. Dr. Panjabi previously hypothesized that for someone without spinal injury there is a normal neutral zone (that part of the range of motion where there is minimal resistance to inter-vertebral motion) with a normal range of motion and, in turn, no spinal pain. In this instance, the bowl is not too deep nor too shallow. However, when an injury occurs to an anatomical structure associated with the spine, the neutral zone of the spinal column increases and "the ball" moves freely over a larger distance. By the noted analogy, the bowl would be shallower and the ball less stable; consequently, pain would result from the enlarged neutral zone.

In general, pedicle screws 16, 18 are used to attach the dynamic spine stabilizing member 10 to the vertebrae 12, 14 of the spine using well-tolerated and familiar surgical procedures known to those skilled in the art. The pedicle screws 16, 18 in combination with a dynamic spine stabilizing member 10 comprise a stabilizing system 11. In accordance with an exemplary embodiment, and as those skilled in the art will certainly appreciate, paired stabilizing systems 11 are commonly used to balance the loads applied to the spine (see FIG. 3c). The dynamic spine stabilizing members 10 assist the compromised (injured and/or degenerated) spine of a back-pain patient, and help her/him perform daily-activities. The dynamic spine stabilizing member 10 does so as part of stabilizing system 11 by providing controlled resistance to spinal motion, particularly around neutral posture in the region of neutral zone. As the spine bends forward (flexion) the stabilizing member 10 is tensioned (see FIG. 3d) and when the spine bends backward (extension) the stabilizing member 10 is compressed (see FIG. 3e).

The resistance to displacement provided by the dynamic spine stabilizing member 10 is non-linear, being greatest in its central zone so as to correspond to the individual's neutral zone; that is, the central zone of the stabilizing member 10 provides a high level of mechanical assistance in supporting the spine. As the individual moves beyond the neutral zone, the increase in resistance decreases to a more moderate level. As a result, the individual encounters greater resistance to movement (or greater incremental resistance) while moving within the neutral zone.

The central zone of the dynamic spine stabilization system 11, that is, the range of motion in which the spine stabilization system 11 provides the greatest incremental resistance to movement, may be adjustable at the time of surgery according to exemplary embodiments of the present disclosure to suit the neutral zone of each individual patient. Thus, according to exemplary embodiments of the present disclosure, the resistance to movement provided by the dynamic spine stabilizing member 10 is adjustable pre-operatively and/or intra-operatively. This adjustability helps to tailor the mechanical properties of the dynamic spine stabilizing system 11 to suit the compromised spine of the individual patient. In addition, according to exemplary embodiments of the present disclosure, the length of the dynamic spine stabilizer 10 may also (or alternatively) be adjustable intra-operatively to suit individual patient anatomy and to achieve desired spinal posture. In such exemplary embodiments, the dynamic spine stabilizing element 10 can be re-adjusted post-operatively with a surgical procedure to adjust its central zone, e.g., to accommodate a patient's altered needs.

Figure 4:
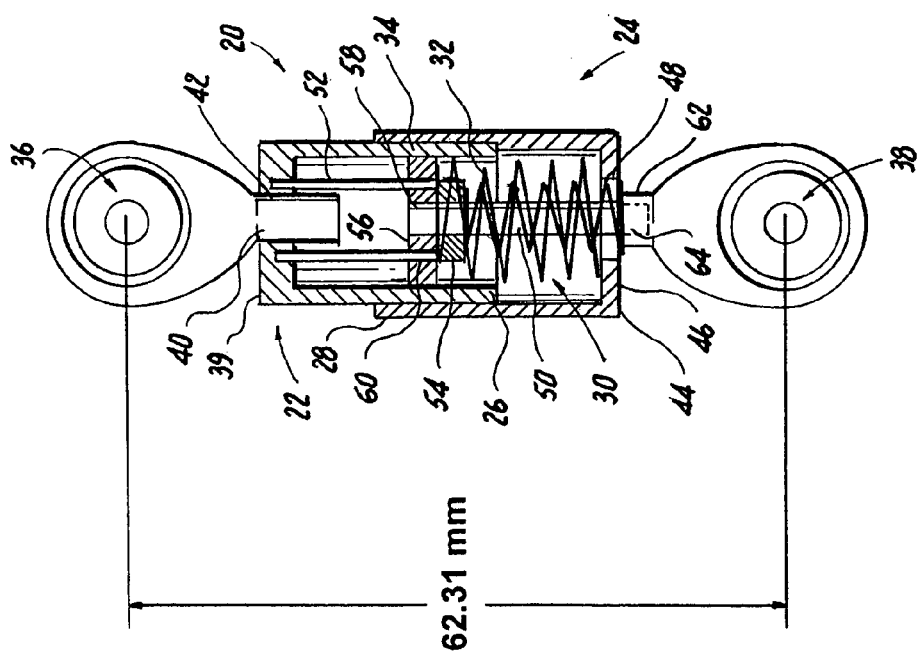
FIG. 4 is a schematic representation of an exemplary dynamic spine stabilizer according to the present disclosure.

With reference to FIG. 4, ball joints 36, 38 may be employed according to exemplary embodiments of the present disclosure to link or otherwise join the dynamic spine stabilizing member 10 with pedicle screws 16, 18. The junction of the dynamic spine stabilizing member 10 and pedicle screws 16, 18 is free and rotationally unconstrained. Thus, three rotational degrees of freedom are provided by advantageous dynamic junctions according to the present disclosure. Alternative structural arrangements are contemplated to provide the desired rotational degrees of freedom of the disclosed dynamic joints, e.g., universal joint structures of the type disclosed in FIG. 29 and discussed herein below. The structures mounted with respect to the pedicle screw that support or accommodate motion relative to the pedicle screw, e.g., the disclosed spherical elements and universal joint mechanisms, are exemplary motion interface elements according to the present disclosure. Therefore, first of all, by providing the dynamic junctions of the present disclosure, the spine is allowed all physiological motions of bending and twisting and, second, the dynamic spine stabilizing member 10 and pedicle screws 16, 18 are protected from potentially harmful bending and/or torsional forces, or moments. As previously stated, while ball joints are disclosed in accordance with an exemplary embodiment of the present disclosure, the present disclosure is not limited to use of one or more ball joints, and other linking structures/mechanisms may be utilized without departing from the spirit or scope of the present disclosure.

As there are ball joints 36, 38 mechanically cooperating with each end of the stabilizing member 10 according to the exemplary embodiment of FIG. 4, bending moments are generally not transferred from the spine to the stabilizing member 10 within stabilizing system 11. Further, it is important to recognize that the only forces associated with operation of stabilizing member 10 are the forces due to the forces of springs 30, 32 that form part of stabilizing member 10. These forces are solely dependent upon the tension and/or compression of the stabilizing member 10 as determined by spinal motion. In summary, the forces associated with operation of stabilizing member 10 are limited to the spring forces. Irrespective of the large loads on the spine, such as when a person carries or lifts a heavy load, the loads experienced by stabilizing member 10 are only associated with the spring forces developed within stabilizing member 10, which are the result of spinal motion and not the result of the spinal load. The stabilizing member 10 is, therefore, uniquely able to assist the spine without enduring the high loads of the spine, allowing a wide range of design options.

The loading of the pedicle screws 16, 18 in the presently disclosed stabilizing system 11 is also quite different from that in prior art pedicle screw fixation devices. The only load experienced by the pedicle screws 16, 18 of stabilizing system 11 is the force delivered by the stabilizing member 10 which translates into pure axial force at the ball joint-screw interface. The design and operation of the disclosed stabilizing system 11 thus greatly reduces the bending moments placed onto pedicle screws 16, 18, as compared to prior art pedicle screw fusion systems. Due to the free motion associated with ball joints 36, 38, the bending moment within each pedicle screw 16, 18 is theoretically zero at ball joints 36, 38, respectively, and the potential for failure is therefore advantageously reduced. In sum, the pedicle screws 16, 18, when used as part of the exemplary dynamic spine stabilization systems of the present disclosure, carry significantly less load and are placed under significantly less stress than typical pedicle screws.

Figure 1:
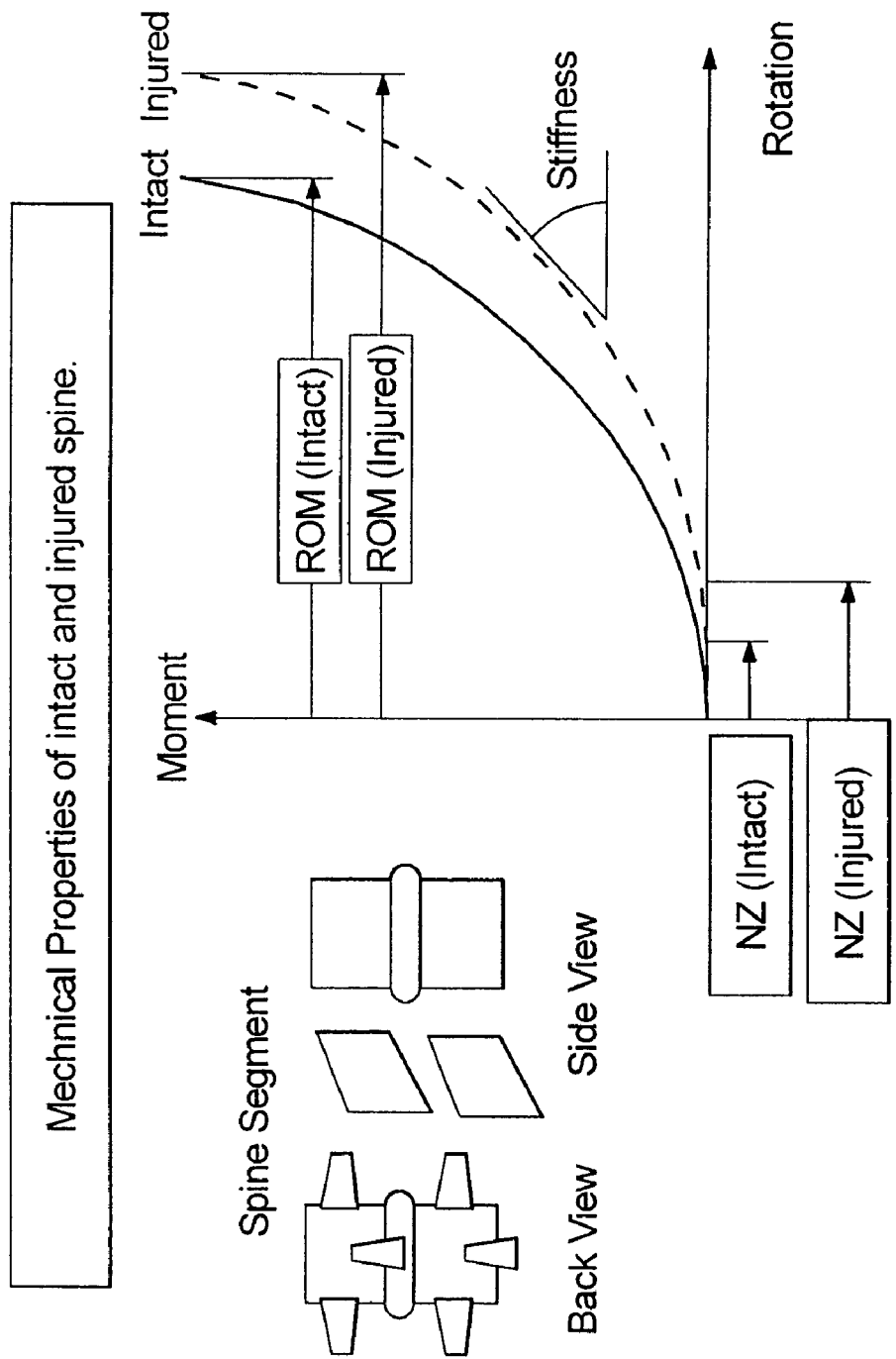
FIG. 1 is a Moment-Rotation curve for a spinal segment (intact and injured), showing relatively low spinal stiffness within the neutral zone.

In FIG. 2, the Moment-Rotation curve for a healthy spine is shown in configurations with an exemplary stabilizing member 10 as part of a dynamic spine stabilizing system. This curve shows the low resistance to movement encountered in the neutral zone of a healthy spine. However, when the spine is injured, this curve changes and the spine becomes unstable, as evidenced by the expansion of the neutral zone (see FIG. 1).

In accordance with exemplary embodiments of the present disclosure, people suffering from spinal injuries are best treated through devices, systems and methods that provide increased mechanical assistance in the neutral zone. As the spine moves beyond the neutral zone, the necessary mechanical assistance decreases and becomes more moderate. In particular, and with reference to FIG. 3a, an exemplary support profile contemplated through implementation of advantageously disclosed devices, systems and methods is depicted.

Figure 3A:
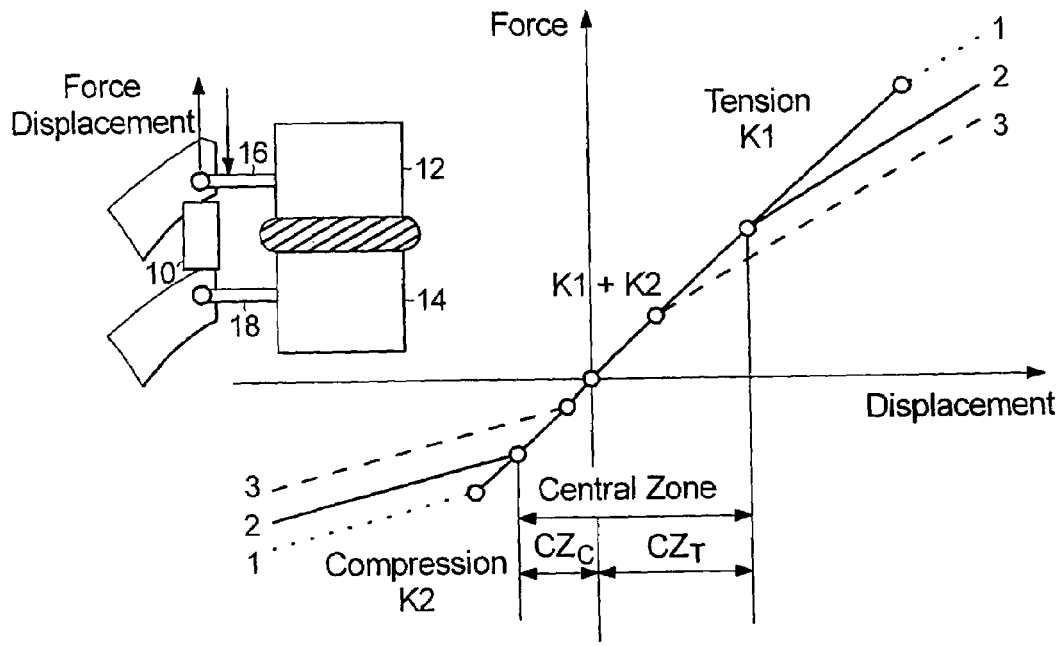
FIG. 3a is a schematic representation of an exemplary device/system according to the present disclosure in conjunction with a Force-Displacement curve, demonstrating increased resistance provided within the central zone of a dynamic spine stabilizer according to the present disclosure.
Figure 3B:
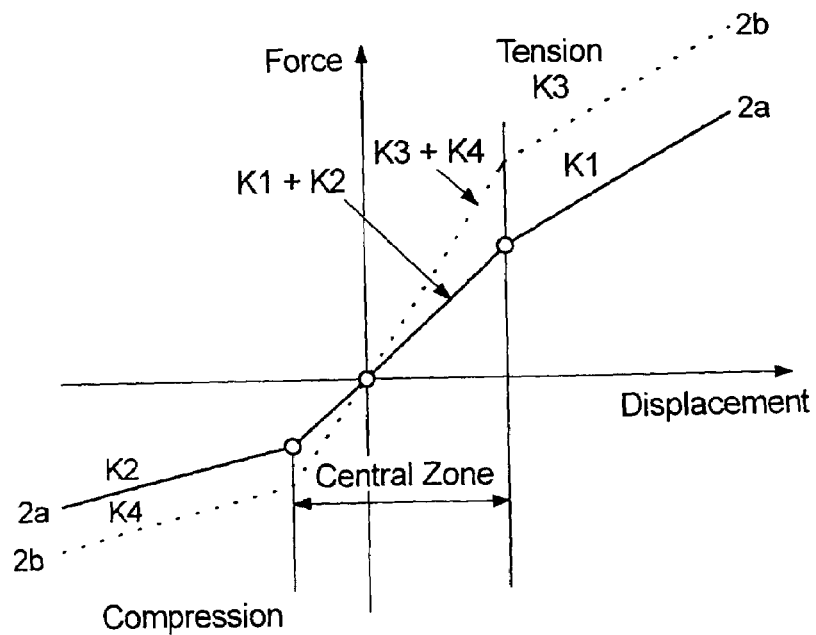
FIG. 3b is a Force-Displacement curve demonstrating a change in profile achieved through replacement of springs according to an exemplary embodiment of the present disclosure.
Figure 3C:
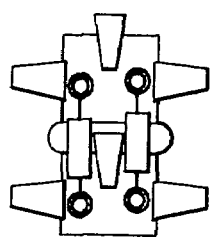
FIG. 3c is a posterior or dorsal view of the spine with a pair of exemplary stabilizers secured thereto.
Figure 3D:
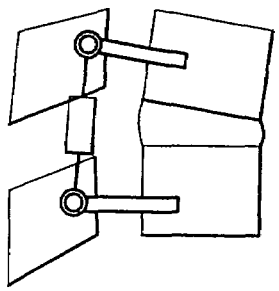
FIG. 3d is a lateral or side view showing an exemplary stabilizer according to the present disclosure in tension.
Figure 3E:
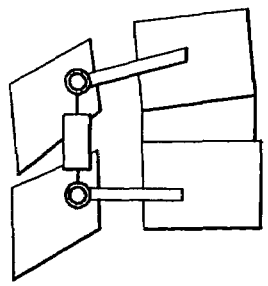
FIG. 3e is a lateral or side view showing an exemplary stabilizer according to the present disclosure in compression.

Three different profiles are shown in FIG. 3a. The disclosed profiles are merely exemplary and demonstrate the possible support requirements within the neutral zone. Profile 1 is exemplary of an individual requiring great assistance in the neutral zone and the central zone of the stabilizing system of the present disclosure is therefore increased, providing a high level of resistance over a great displacement; Profile 2 is exemplary of an individual where less assistance is required in the neutral zone and the central zone of the stabilizing system of the present disclosure is therefore more moderate, providing increased resistance over a more limited range of displacement; and Profile 3 is exemplary of situations where only slightly greater assistance is required in the neutral zone and the central zone of the stabilizing system of the present disclosure may therefore be decreased to provide increased resistance over even a smaller range of displacement.

As those skilled in the art will certainly appreciate, the mechanical assistance required and the range of the neutral zone will vary from individual to individual. However, the basic tenet of the present invention remains; that is, greater mechanical assistance for those individuals suffering from spinal instability is required within the individual's neutral zone. This assistance is provided in the form of greater resistance to movement provided within the neutral zone of the individual and the central zone of the dynamic spine stabilizing member 10 which advantageously forms part of a dynamic spine stabilizing system.

Exemplary dynamic spine stabilizing member 10 of the present disclosure advantageously provides mechanical assistance in accordance with the desired support profile. Further, exemplary embodiments of dynamic spine stabilizing member 10 provide for adjustability, e.g., via a concentric spring design. More specifically and with reference to exemplary embodiments of the present disclosure, spine stabilizing system 10 provides assistance to the compromised spine in the form of increased stiffness, i.e., greater incremental resistance to movement (provided by springs in accordance with a preferred embodiment) as the spine moves from the neutral posture, in any physiological direction. As mentioned above, the Force-Displacement relationship provided by exemplary stabilizing system 10 and dynamic spine stabilizing member 10 are non-linear, with greater incremental resistance around the neutral zone of the spine and central zone of the stabilizing system 11, and decreasing incremental resistance beyond the central zone of the dynamic spine stabilizing system 11 as the individual moves beyond the neutral zone (see FIG. 3a).

The relationship of the present stabilizing system 11 to forces applied during tension and compression is further shown with reference to FIG. 3a. As discussed above, the behavior of the present stabilizing system 11 is non-linear. The Load-Displacement curve has three zones: tension, central and compression. If K1 and K2 define the stiffness values in the tension and compression zones, respectively, the advantageous stabilizing systems according to the present disclosure are designed such that high stiffness is delivered in the central zone, i.e., "K1+K2". Depending upon the "preload" of stabilizing member 10, as discussed below in greater detail, the width of the central zone and, therefore, the region of high stiffness, can be adjusted.

With reference to FIG. 4, an exemplary dynamic spine stabilizing system 11 that includes a dynamic spine stabilizing member 10 in accordance with the present disclosure is schematically depicted. Dynamic spine stabilizing system 11 includes a support assembly associated with spine stabilizing member 10 in the form of a housing 20 composed of a first housing member 22 and a second housing member 24. The first housing member 22 and the second housing member 24 are telescopically connected via external threads formed upon the open end 26 of the first housing member 22 and internal threads formed upon the open end 28 of the second housing member 24. In this way, the housing 20 is completed by screwing the first housing member 22 into the second housing member 24. As such, and as will be discussed below in greater detail, the relative distance between the first housing member 22 and the second housing member 24 can be readily adjusted for the purpose of adjusting the compression of first spring 30 and second spring 32 contained within the housing 20. Although springs are employed in accordance with a preferred embodiment of the present invention, other elastic members may be employed without departing from the spirit or scope of the present invention. A piston assembly 34 links the first spring 30 and the second spring 32 relative to first and second ball joints 36, 38. The first and second ball joints 36, 38 are in turn shaped and designed for selective attachment to pedicle screws 16, 18, which may extend from the respective vertebrae 12, 14 (as shown, e.g., in FIG. 2).

The first ball joint 36 is secured relative to the closed end 39 of the first housing member 22 via a threaded engagement member 40 that is shaped and dimensioned for coupling with first housing member 22. According to an exemplary embodiment of the present disclosure, an aperture 42 is formed in the closed end 39 of the first housing member 22 and is provided with threads for engaging the threaded portion of engagement member 40. In this way, the first ball joint 36 substantially closes off the closed end 39 of the first housing member 22. The length of dynamic spine stabilizing system 11 may be readily adjusted by rotating the first ball joint 36 relative to first housing member 22 to adjust the extent of overlap between the first housing member 22 and the engagement member 40 of the first ball joint 36, i.e., the degree to which engagement member 40 is nested within first housing member 22. As those skilled in the art will certainly appreciate, a threaded engagement between the first housing member 22 and the engagement member 40 of the first ball joint 36 is disclosed in accordance with an exemplary embodiment of the present disclosure, although other coupling structures (e.g., welding attachment, a bayonet lock or the like) may be employed without departing from the spirit or scope of the present invention.

In an exemplary embodiment of the present disclosure, the closed end 44 of the second housing member 24 is provided with a cap 46 having an aperture 48 formed therein. As will be discussed below in greater detail, the aperture 48 is shaped and dimensioned to accommodate passage of a piston rod 50 associated with piston assembly 34 therethrough. Exemplary piston assembly 34 includes a piston rod 50; first and second springs 30, 32; and retaining rods 52. The piston rod 50 includes a stop nut 54 and an enlarged head 56 at its first end 58. The enlarged head 56 is rigidly connected to the piston rod 50 and includes guide holes 60 through which the retaining rods 52 extend during operation of the present dynamic spine stabilizing member 10. As such, the enlarged head 56 is guided along the retaining rods 52 while the second ball joint 38 moves toward and away from the first ball joint 36, i.e., in connection with relative motion between first and second ball joints 36, 38. As will be discussed below in greater detail, the enlarged head 56 interacts with the first spring 30 to create resistance as the dynamic spine stabilizing member 10 is extended and the spine is moved in flexion.

A stop nut 54 is fit over the piston rod 50 for free movement relative thereto. However, movement of the stop nut 54 toward the first ball joint 36 is prevented by the retaining rods 52 that support the stop nut 54 and prevent the stop nut 54 from moving toward the first ball joint 36. As will be discussed below in greater detail, the stop nut 54 interacts with the second spring 32 to create resistance as the dynamic spine stabilizing member 10 is compressed and the spine is moved in extension.

The second end 62 of the piston rod 50 extends from the aperture 48 at the closed end 44 of the second housing member 24, and is attached to an engagement member 64 associated with the second ball joint 38. In an exemplary embodiment of the present disclosure, the second end 62 of the piston rod 50 is coupled to the engagement member 64 of the second ball joint 38 via a threaded engagement. As those skilled in the art will certainly appreciate, a threaded engagement between the second end 62 of the piston rod 50 and the engagement member 64 of the second ball joint 38 is disclosed in accordance with an exemplary embodiment, although other coupling structures may be employed without departing from the spirit or scope of the present invention.

As briefly mentioned above, first and second springs 30, 32 are held or captured within housing 20. In particular, the first spring 30 extends between the enlarged head 56 of the piston rod 50 and the cap 46 of the second housing member 24. The second spring 32 extends between the distal end of the engagement member 64 of the second ball joint 38 and the stop nut 54 of the piston rod 50. A preloaded force applied by the first and second springs 30, 32 generally holds the piston rod in a static position within the housing 20, and the piston rod 50 is able to move relative to housing 20 during either extension or flexion of the spine.

In use, when the vertebrae 12, 14 are moved in flexion and the first ball joint 36 is drawn away from the second ball joint 38, i.e., there is relative motion between first and second ball joints 36, 38 such that they are moving away from each other, the piston rod 50 is pulled within the housing 24 against the force being applied by the first spring 30. In particular, the enlarged head 56 of the piston rod 50 is moved toward the closed end 44 of the second housing member 24. This movement causes compression of the first spring 30, creating resistance to the movement of the spine. With regard to the second spring 32, the second spring 32 moves with the piston rod 50 away from second ball joint 38. As the vertebrae move in flexion within the neutral zone, the height of the second spring 32 is increased, reducing the distractive force, and in effect increasing the resistance of the device to movement. Through this mechanism, as the spine moves in flexion from the initial position both spring 30 and spring 32 resist the distraction of the device directly, either by increasing the load within the spring (i.e. first spring 30) or by decreasing the load assisting the motion (i.e. second spring 32).

However, when the spine is in extension, and the second ball joint 38 is moved toward the first ball joint 36, the engagement member 64 of the second ball joint 38 moves toward the stop nut 54, which is held in place by the retaining rods 52 as the piston rod 50 moves toward the first ball joint 36. This movement causes compression of the second spring 32 held between the engagement member 64 of the second ball joint 38 and the stop nut 54, to create resistance to the movement within the dynamic spine stabilizing member 10. With regard to the first spring 30, the first spring 30 is supported between the cap 46 and the enlarged head 56, and as the vertebrae move in extension within the neutral zone, the height of the second spring 32 is increased, reducing the compressive force, and in effect increasing the resistance of the device to movement. Through this mechanism, as the spine moves in extension from the initial position both spring 32 and spring 30 resist the compression of the device directly, either by increasing the load within the spring (i.e. second spring 32) or by decreasing the load assisting the motion (i.e. first spring 30).

Based upon the use of two concentrically positioned elastic springs 30, 32 as disclosed in accordance with an exemplary embodiment of the present invention, an assistance (force) profile as shown in FIG. 2 is provided by the present dynamic spine stabilizing member 10. That is, the first and second springs 30, 32 work in conjunction to provide a large elastic force when the dynamic spine stabilizing member 10 is displaced within the central zone of the stabilizing system 11. However, once displacement between the first ball joint 36 and the second ball joint 38 extends beyond the central zone of the stabilizing system 11 and the neutral zone of the individual's spinal movement, the incremental resistance to motion is substantially reduced as the individual no longer requires the substantial assistance needed within the neutral zone. This is accomplished by setting the central zone of the device disclosed herein. The central zone of the force displacement curve is the area of the curve, which represents when both springs are acting in the device as described above. When the motion of the spine is outside the neutral zone and the correlating device elongation or compression is outside the set central zone, the spring, which is elongating, reaches its free length. Free length, as anybody skilled in the art will appreciate, is the length of a spring when no force is applied. In the advantageous, exemplary mechanism of the present disclosure, the resistance to movement of the device outside the central zone (where both springs are acting to resist motion) is only reliant on the resistance of one spring: either spring 30 in flexion or spring 32 in extension.

As briefly discussed above, exemplary dynamic spine stabilizing member 10 may be adjusted by rotation of the first housing member 22 relative to the second housing member 24. This movement changes the distance between the first housing member 22 and the second housing member 24 in a manner which ultimately changes the preload placed across the first and second springs 30, 32. This change in preload alters the resistance profile of the present dynamic spine stabilizing member 10 from that shown in Profile 2 of FIG. 3a to an increase in preload (see Profile 1 of FIG. 3a), which enlarges the effective range in which the first and second springs 30, 32 act in unison. This increased width of the central zone of the stabilizing member 10 correlates to higher stiffness over a larger range of motion of the spine. This effect can be reversed, as is evident in Profile 3 of FIG. 3a.

The present dynamic spine stabilizing member 10 is attached to pedicle screws 16, 18 extending from the vertebral section requiring support. During surgical attachment of the dynamic spine stabilizing member 10, the magnitude of the stabilizer's central zone can be adjusted for each individual patient according to exemplary embodiments of the present disclosure, as judged by the surgeon and/or quantified by an instability measurement device. This adjustable feature of the dynamic spine stabilizing member 10 is exemplified in the three explanatory profiles that have been generated in accordance with an exemplary embodiment of the present invention (see FIGS. 3a and 3b; note the width of the device central zones).

Pre-operatively, the first and second elastic springs 30, 32 of the dynamic spine stabilizing member 10 can be replaced by a different set of springs (in whole or in part) to accommodate a wider range of spinal instabilities. As expressed in FIG. 3b, Profile 2b demonstrates the force displacement curve generated with a stiffer set of springs when compared with the curve shown in Profile 2a of FIG. 3b.

Intra-operatively, the length of exemplary dynamic spine stabilizing member 10 may be adjustable, e.g., by turning engagement member 40 of the first ball joint 36 to lengthen the stabilizing member 10 in order to accommodate different patient anatomies and desired spinal posture. Pre-operatively, the piston rod 50 may be replaced with piston rods of differing lengths/geometries to accommodate an even wider range of anatomic variation.

The exemplary dynamic spine stabilizing member 10 disclosed herein has been tested alone for its load-displacement relationship. When applying tension, the dynamic spine stabilizing member 10 demonstrated increasing resistance up to a pre-defined displacement, followed by a reduced rate of increasing resistance until the device reached its fully elongated position. When subjected to compression, the dynamic spine stabilizing member 10 demonstrated increasing resistance up to a pre-defined displacement, followed by a reduced rate of increasing resistance until the device reached its fully compressed position. Therefore, the dynamic spine stabilizing member 10 exhibits a load-displacement curve that is non-linear with the greatest resistance to displacement offered around the neutral posture. This advantageous behavior helps to normalize the load-displacement curve of a compromised spine.

Figure 5:
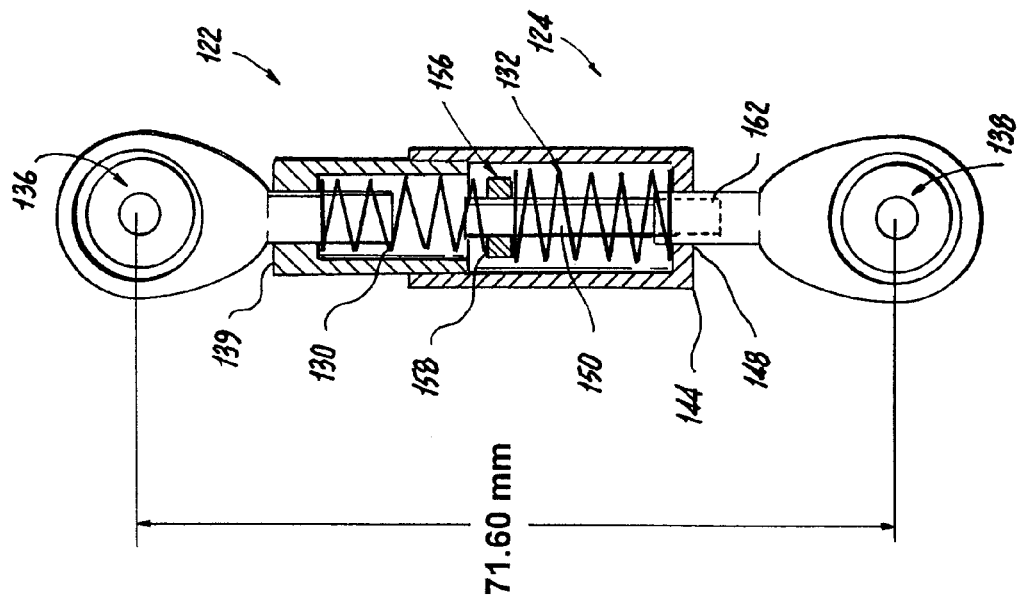
FIG. 5 is a schematic representation of an alternate exemplary embodiment of a dynamic spine stabilizer in accordance with one aspect of the present disclosure.

In another exemplary embodiment of the present disclosure, with reference to FIG. 5, the stabilizing member 110 may be constructed with an in-line spring arrangement. In accordance with this embodiment, the housing 120 is composed of first and second housing members 122, 124 which are coupled with threads allowing for adjustability. A first ball joint 136 extends from or relative to the first housing member 122. The second housing member 124 is provided with an aperture 148 through which the second end 162 of piston rod 150 extends. The second end 162 of the piston rod 150 is attached relative to the second ball joint 138. For example, the second ball joint 138 may be screwed onto the piston rod 150.

The piston rod 150 includes an enlarged head 156 at its first end 158. The first and second springs 130, 132 are respectively secured between the enlarged head 156 and the closed ends 139, 144 of the first and second housing members 122, 124. In this way, the stabilizing member 110 provides resistance to both expansion and compression using the same mechanical principles described for the previous embodiment, i.e., stabilizing member 10.

Adjustment of the resistance profile in accordance with this alternate embodiment may be achieved by rotating the first housing member 122 relative to the second housing member 124. Rotation in this way alters the central zone of high resistance provided by stabilizing member 110. As previously described, one or both springs may also be exchanged to change the slope of the force-displacement curve in two or three zones, respectively.

Figure 6:
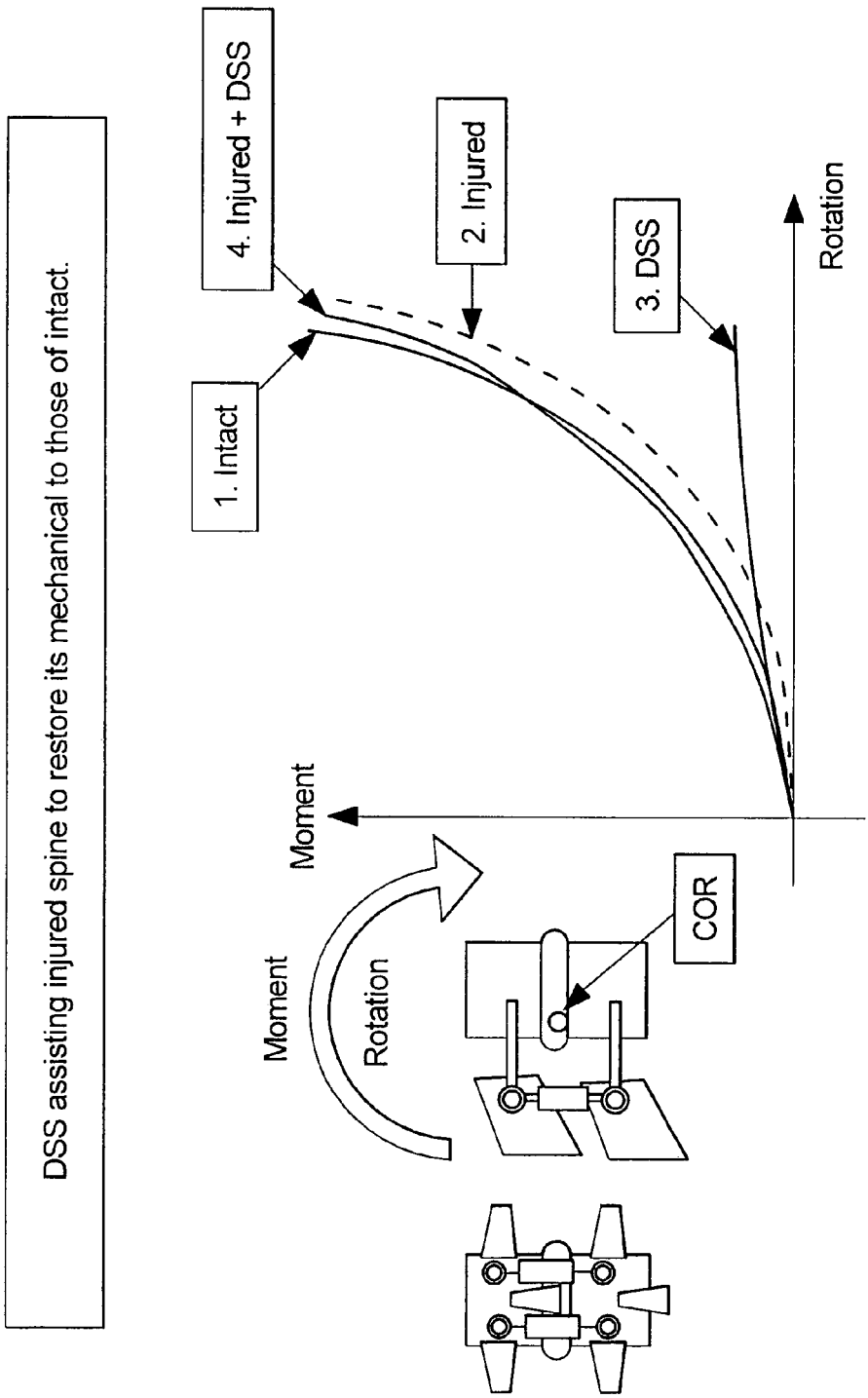
FIG. 6 is a Moment-Rotation curve demonstrating the manner in which an exemplary dynamic spine stabilizer according to the present disclosure assists spinal stabilization.

To explain how the exemplary stabilizing members 10, 110 assist a compromised spine (increased support in the neutral zone), reference is made to the moment-rotation curves (FIG. 6). Four curves are shown: 1. Intact, 2. Injured, 3. Stabilizer ("DSS") and, 4. Injured+Stabilizer ("DSS"). These are, respectively, the Moment-Rotation curves of the intact spine, injured spine, stabilizer alone, and stabilizer plus injured spine. Of note, the latter curve (i.e., injured spine plus stabilizing system of the present disclosure) is close to the intact curve. Thus, the stabilizer/stabilizing system of the present disclosure, which provides greater resistance to movement around the neutral posture, is well suited to compensate for the instability of the spine.

With reference to FIGS. 8 to 17, further embodiments of the advantageous stabilizing system 211 of the present disclosure (and associated force profile characteristics) are schematically depicted and described herein. This exemplary stabilizing system 211 includes first and second concentric springs 212, 214 as part of stabilizing member 210 that is positioned between first and second pedicle screws 216, 218, as generally shown in the exploded view of FIG. 8. As those skilled in the art will appreciate, the springs that are incorporated in stabilizing member 210 may take a variety of forms known to those skilled in the art, for example, machine springs, wire coil springs, wave springs, and the like, without departing from the spirit or scope of present the invention. In addition, it is contemplated that other resistance devices may be incorporated in stabilizing member 210, for example, elastomeric materials and/or elastomeric structures, Belleville washers, and the like (such alternative resistance devices being used alone or in combination with the foregoing springs), without departing from the spirit or scope of the present invention.

Stabilizing system 211 generally defines a first end 220 and a second end 222. The schematic depiction of FIG. 8 includes a pair of pedicle screws (216, 218), but it is to be understood that the "first end" and/or the "second end" may form intermediate locations, with additional pedicle screw and/or stabilizing members positioned therebeyond. Toward the first end 220, a first attachment member 224 is provided that is configured and dimensioned to receive a first ball (or spherical element) 236 to define a first ball joint 226 that accommodates relative movement between the first attachment member 224 and pedicle screw 216. Indeed, the dynamic junction formed at ball joint 226 advantageously provides three rotational degrees of freedom. Toward the second end 222 of stabilizing system 211, a second attachment member 228 is provided that is configured and dimensioned to receive a second ball (or spherical element) 238 to define a second ball joint 230. The second ball joint advantageously accommodates relative movement between the second attachment member 228 and pedicle screw 218, i.e., defines a dynamic junction that provides three rotational degrees of freedom.

Figure 8:
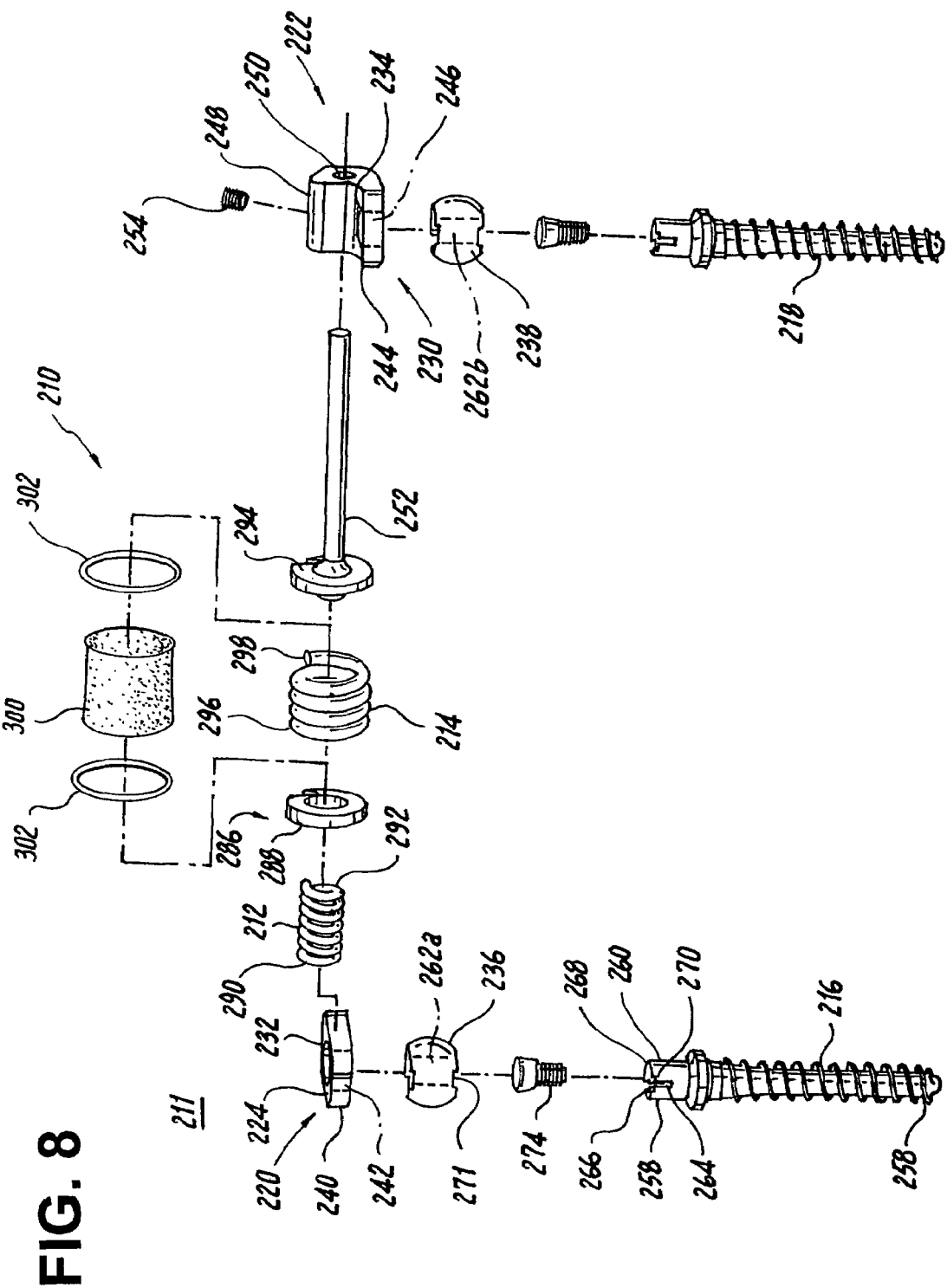
FIG. 8 is an exploded view of an exemplary dynamic spine stabilization system in accordance with an embodiment of the present disclosure.

In the exemplary embodiment of FIG. 8, ball joints 226, 230 include a socket 232, 234 formed integrally with the respective first and second attachment members 224, 228 and a ball or sphere 236, 238 positioned therein. Of course, sockets 232, 234 may be fabricated as separate components from first and second attachment members 224, 228 without departing from the spirit or scope of the present disclosure. In implementations wherein the sockets are fabricated separately from the attachment members, appropriate mechanisms for joining/connection such sub-assemblies may be employed, e.g., welded connections, threaded engagements, bayonet locking mechanisms or the like.

Figure 15A:
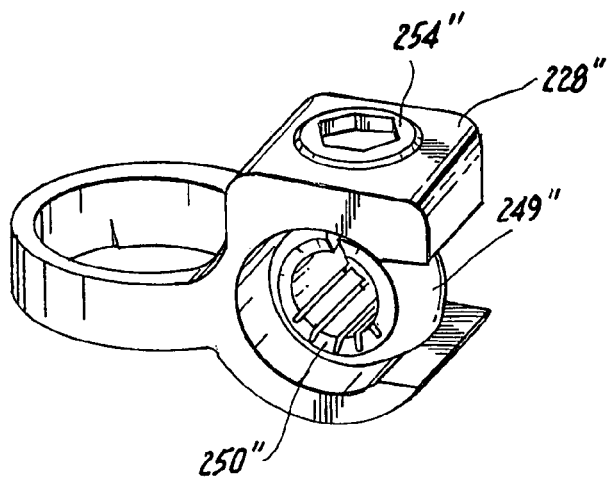
FIG. 15a is a perspective view of an attachment member that is adapted to facilitate alignment with elongated member(s), e.g., rod(s), according to exemplary embodiments of the present disclosure.
Figure 15B:
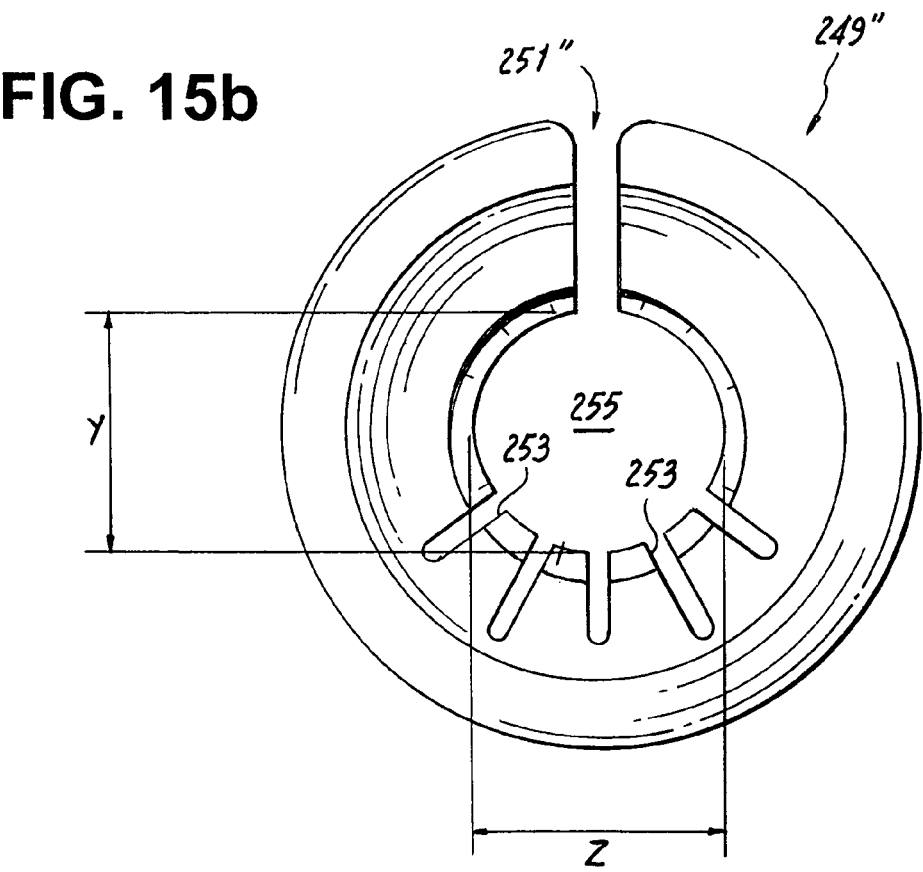
FIG. 15b is a side view of a spherical element for use in an attachment member according to an exemplary embodiment of the present disclosure.
Figure 16:
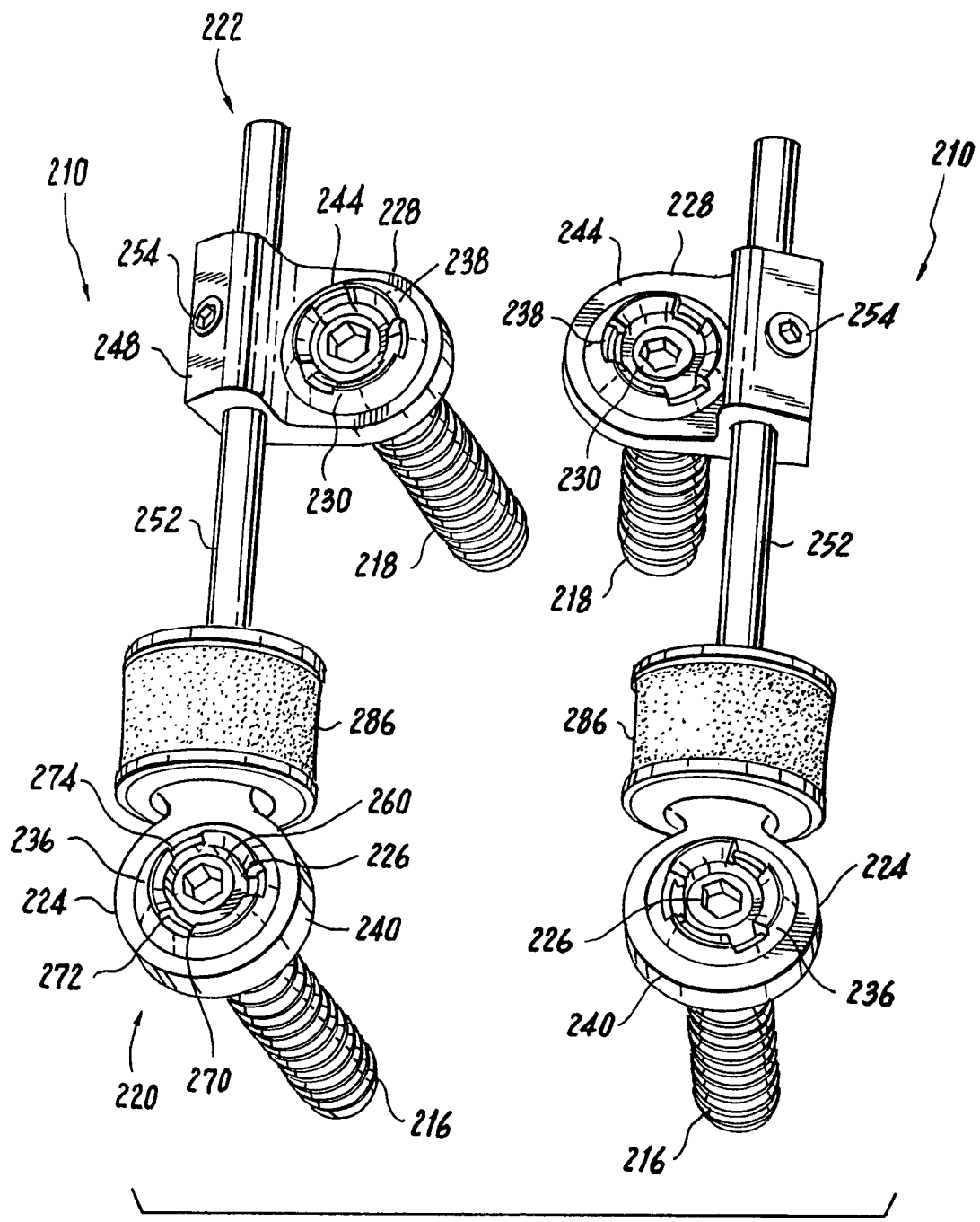
FIG. 16 is a top view of a pair of single level spinal stabilization systems according to an exemplary embodiment of the present disclosure.
Figure 28:
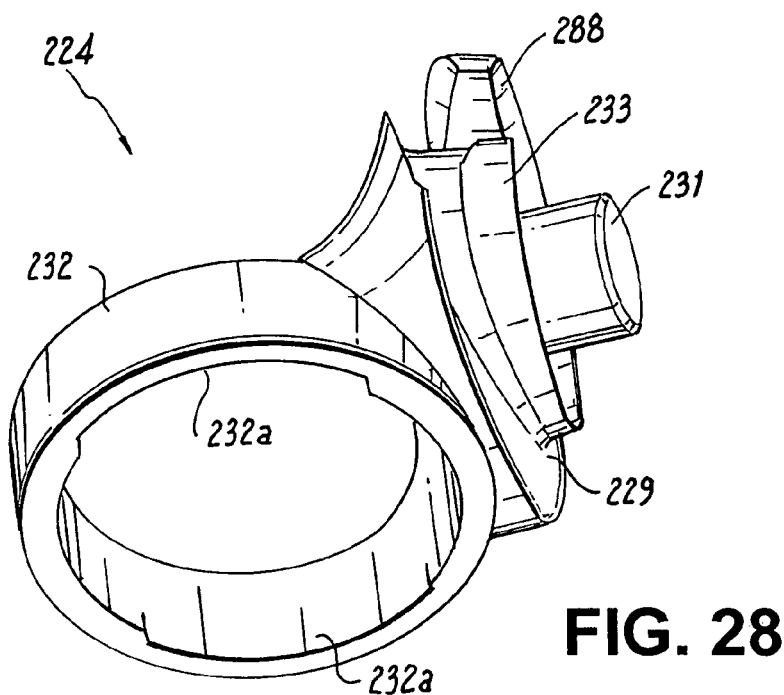
FIG. 28 is a perspective view of an exemplary socket member and spring cap according to an exemplary embodiment of the present disclosure.

According to the exemplary embodiment of FIGS. 8-17, the first attachment member 224 is structured for supporting the inner first spring 212 for operation in accordance with the present stabilizing system 211. As best seen in FIGS. 16 and 28, the first attachment member 224 includes a body member 240 having an aperture 242 extending therethrough. The inner surface of aperture 242 defines socket 232 and is shaped and dimensioned for receipt of ball (or spherical element) 236. The assembly of the ball/spherical element is achieved by rotating the ball 90 degrees off of the normal position of the ball relative to socket 232. At this position the ball/spherical element can slide through two opposed slots 232a cut in the internal spherical race of the socket. In exemplary embodiments of the present disclosure, the opposed slots are substantially arcuate and extend for a distance that accommodates the height of the spherical element. Once positioned within the socket, the ball/spherical element is generally rotated relative to the socket to prevent disengagement therefrom. Indeed, once assembled onto the pedicle screw, there is no possibility of the ball/spherical element coming disassembled from the internal spherical race formed in the socket member. In exemplary embodiments of the present disclosure, aperture 242 is sized such that ball/spherical element 236 engages socket 232 at or near a plane that defines the diameter of ball/spherical element 236. In this way, ball/spherical element 236 is centrally positioned relative to socket 232 and is not permitted to pass through socket 232. The inner first spring 212 extends from, and in an exemplary embodiment is integrally formed with, the body member 240 of the first attachment member 224.

The second attachment member 228 similarly includes a body member 244 having an aperture 246 extending therethrough. The inner surface of the aperture 246 defines a socket 234 that is shaped and dimensioned for receipt of the ball 238. Thus, in exemplary embodiments, socket 234 includes opposed slots to accommodate introduction of a ball/spherical element, as described above with reference to socket 232. As with the dimensional relationship between ball 236 and socket 232, aperture 246 is advantageously dimensioned such that ball 238 is engaged by socket 232 at or near a plane that defines the diameter of ball 238 (and ball 238 is not permitted to pass through socket 232). The second attachment member 228 further includes a rod connector 248 with a transverse aperture or channel 250 extending therethrough. The transverse aperture or channel 250 is shaped and dimensioned for passage of spring cap rod 252 therethrough. The spring cap rod 252 is secured within the transverse aperture 250, e.g., via a set screw 254 extending through a threaded aperture that provides a channel from the external surface of the rod connector 248 and the transverse aperture/channel 250 within which is positioned spring cap rod 252.

Figure 10:
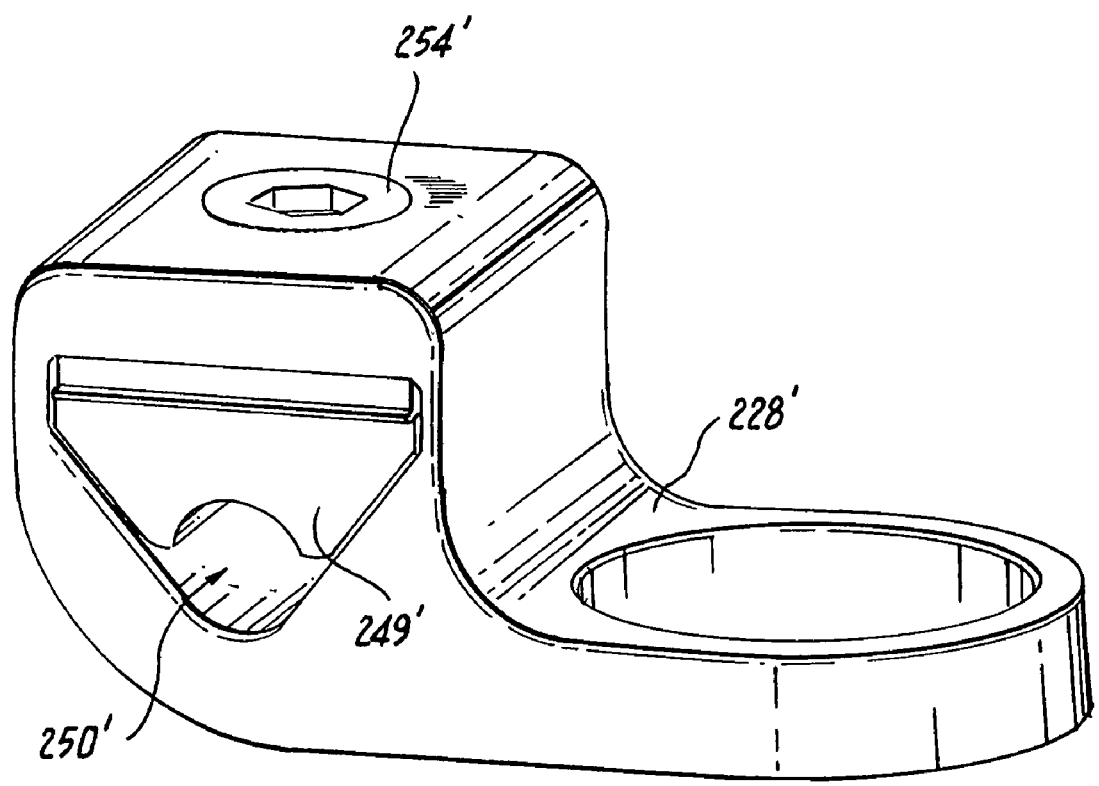
FIGS. 10 and 11 are perspective views showing exemplary attachment members for use with dynamic spine stabilizations of the present disclosure.

In accordance with an alternate embodiment, and with reference to FIG. 10, set screw 254' interacts with a wedge member 249'. The wedge member 249' is seated within transverse aperture/channel 250' and is shaped and dimensioned for engaging the spring cap rod 252 as it passes through the transverse aperture/channel 250'. More particularly, the wedge member 249' includes an exposed arcuate surface that is shaped and dimensioned to interact with spring cap rod 252' to substantially prevent movement of the spring cap rod relative to the second attachment member 228' when set screw 254' is tightened against wedge member 249'.

Figure 11:
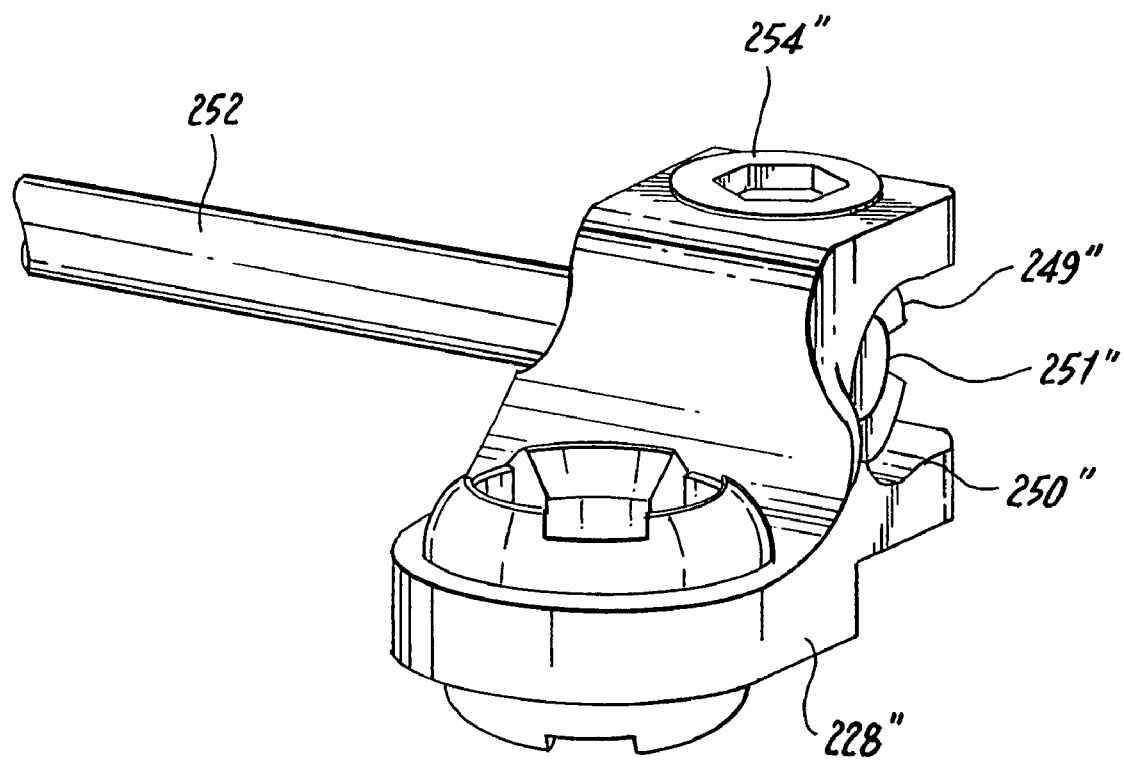
Figure 12:
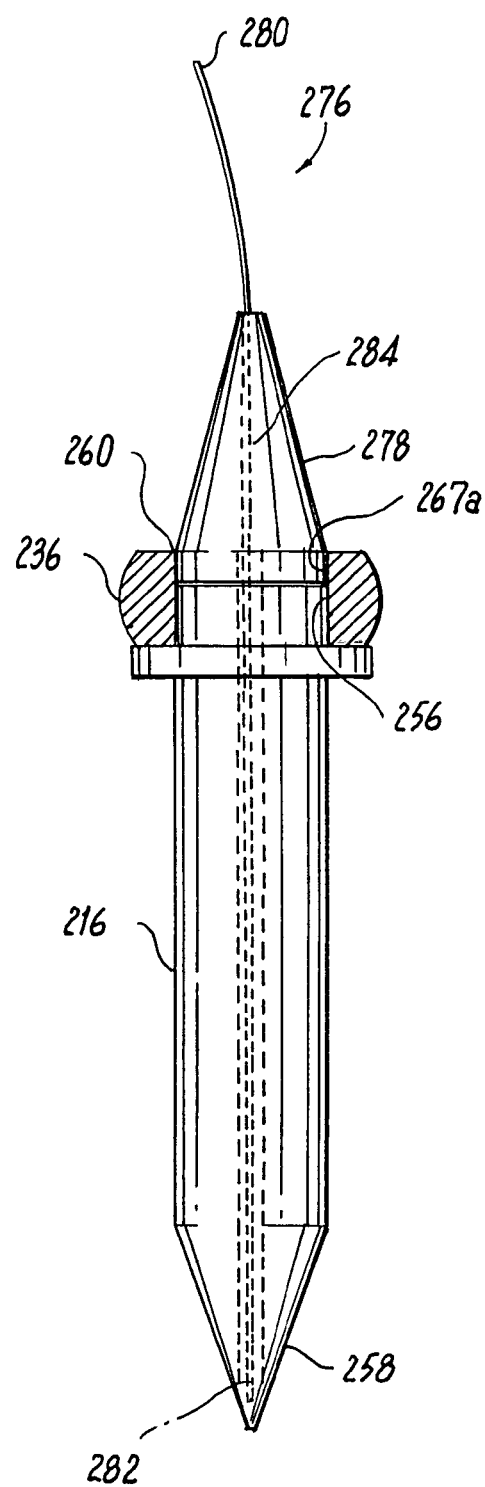
FIG. 12 is a schematic representation showing a guidewire assembly technique in accordance with an exemplary implementation of the spine stabilization techniques of the present disclosure.
Figure 13:
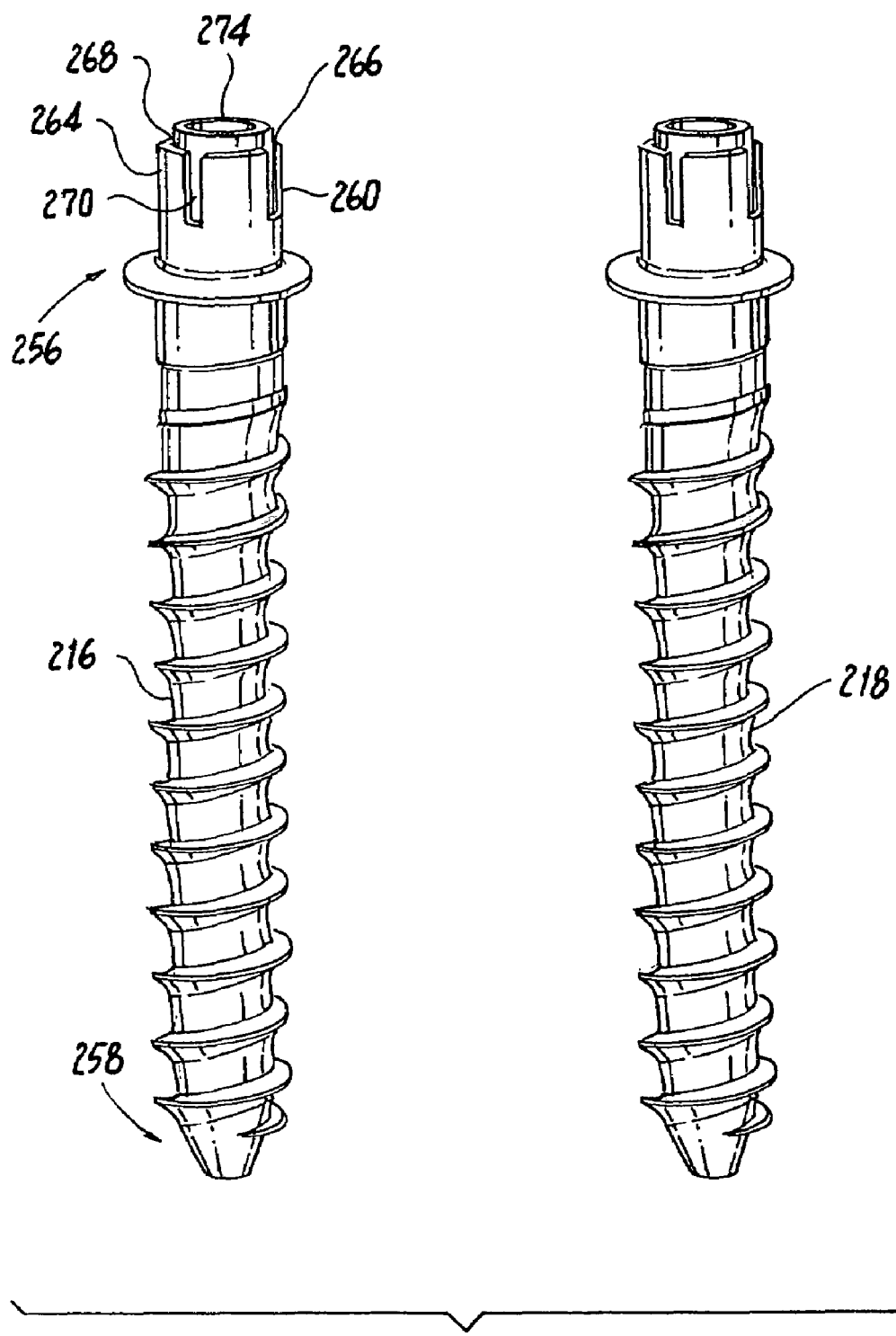
FIG. 13 is a schematic side view of a pair of pedicle screws according to an exemplary embodiment of the present disclosure.
Figure 14:
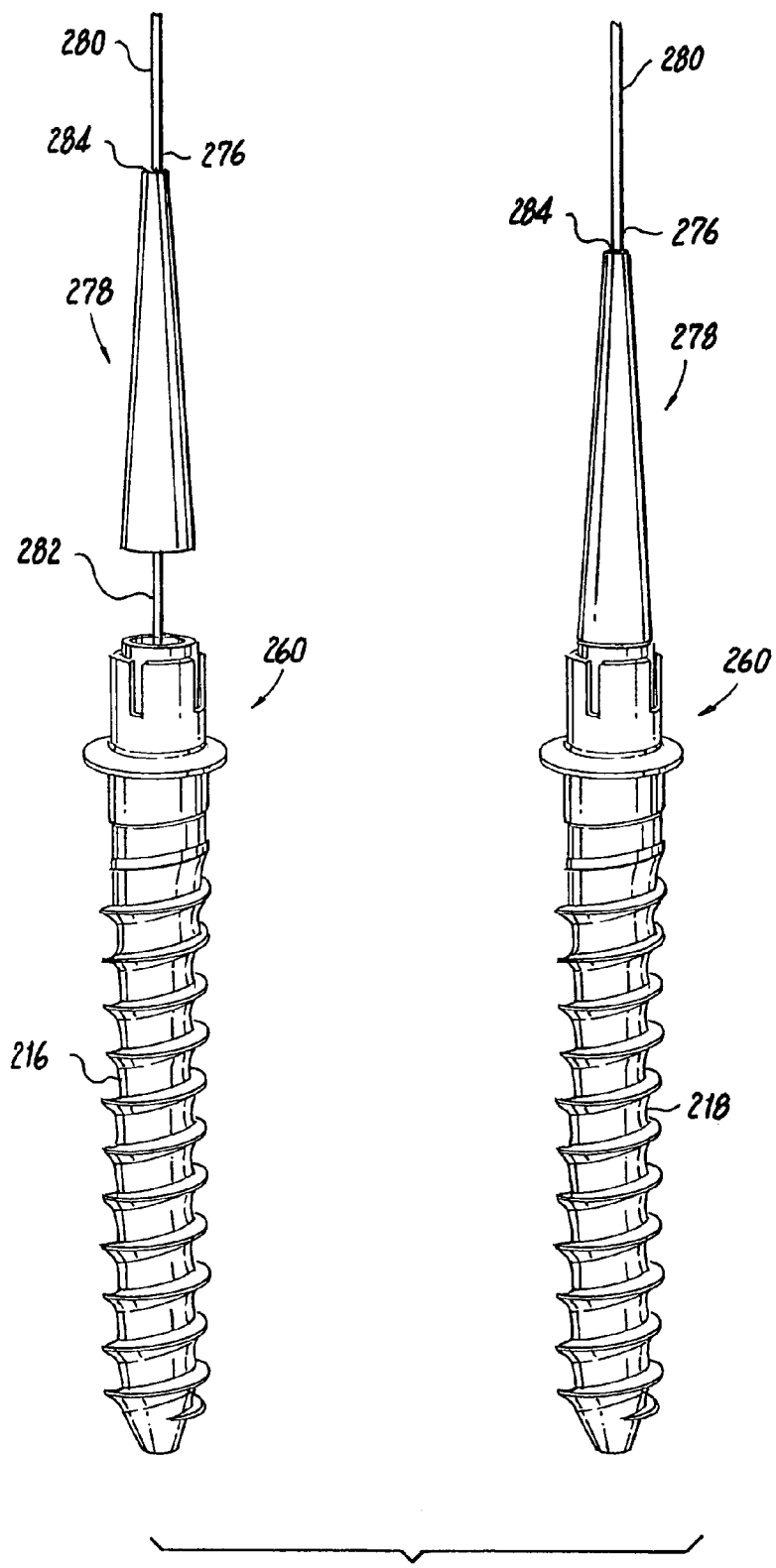
FIG. 14 is a side view of a pair of pedicle screws in combination with guidewire assemblies according to an exemplary embodiment of the present disclosure.

With reference to FIGS. 11, 15a and 15b, a further alternative structural arrangement for securing a spring cap rod relative to an attachment member according to the present disclosure is schematically depicted. The structural arrangement of FIGS. 11, 15a and 15b may be particularly advantageous when it is desirable to provide flexible loading of the spring cap rod within the attachment member. The alternate embodiment of FIGS. 11, 15a and 15b employs a selectively rotatable ball 249" within transverse aperture/channel 250" defined in attachment member 228". The ball 249" includes a transverse compression slot 251" extending therethrough. A plurality of internal grooves 253 opening into opening 255 are also formed in ball 249" to further facilitate gripping of a spring cap rod 252" positioned therewithin, as described in greater detail below. Of note, opening 255 formed in ball 249" and shown in FIG. 15b is advantageously elliptical in geometry, with a minor axis "Y" and a major axis "Z". Compression slot 251" is substantially aligned with the minor axis "Y" and grooves 253 are deployed in an arcuate manner in facing relation to compression slot 251", i.e., on the opposite side of opening 255.

In use, after an element is positioned within opening 255, e.g., an elongated member such as a rod, a mechanism (e.g., set screw 254") is used to apply a force to the exterior of ball 249". The force is advantageously applied to ball 249" in substantial alignment with the major axis "Z" of elliptical opening 255. As force is applied to the outer surface of ball 249", the elliptical opening 255 is deformed and assumes a circular (or substantially circular) geometry. Deformation into a circular geometry is facilitated by the positioning of compression slot 251" and grooves 253 relative to opening 255. Indeed, the positioning of compression slot 251" and grooves 253 accommodates preferential deformation of ball 249" to a desired circular (or substantially circular) opening 255. By assuming a circular/substantially circular geometry, the inner wall of ball 249" around opening 255 engages an elongated member/rod of circular cross section around substantially the entire circumference of the elongated member/rod. By engaging the elongated member/rod around substantially the entire circumference thereof, greater security is imparted between the ball and the elongated member/rod.

Thus, the slot 251" and grooves 253 allow the ball 249" to be compressed and deformed to a limited degree by force imparted by the set screw 254", thereby locking the ball 249" and spring cap rod 252" in position within the transverse aperture/channel 250". The ball 249" allows the spring cap rod 252" to extend therethrough while the orientation of the ball 249" and spring cap rod 252" relative to the second attachment member 228" is adjusted to a desired orientation. Stated differently, ball 249" has three degrees of rotational freedom within aperture/channel 250" such that the ball 249" can be oriented at essentially any angle to accommodate alignment with spring cap rod 252" (or another elongated member/rod), thereby greatly enhancing the ease and flexibility of assembly associated with a spinal stabilization system. Indeed, a rod positioned within ball 249" is generally trimmed-to-length by a clinician/surgeon once assembled with an attachment member; if trimmed very close to the exiting edge of ball 249", the ball/rod combination will exhibit essentially 180° of rotational freedom relative to attachment member 228". High degrees/levels of angulation, as are accommodated by the exemplary embodiments disclosed herein, are generally advantageous in clinical applications. The combination of ball 249" with aperture/channel 250" of attachment member 228" may be termed a "ball-in-a-box." Once the desired orientation is achieved for the rod relative to other components of a spinal stabilization system, the set screw 254" may be tightened and the assembly is thereby locked in position.

With further reference to FIG. 8, the first and second attachment members 224, 228 are adapted to be mounted upon pedicle screws 216, 218. Each of the pedicle screws 216, 218 includes a proximal end 256 and a distal end 258 (inasmuch as the first and second pedicle screws 216, 218 in the exemplary embodiment depicted herein are identical, the same numeric designations will be used in describing both pedicle screws; however, it is contemplated that pedicle screws having differing structural and/or functional features may be incorporated into stabilizing system implementations according to the present disclosure without departing from the spirit or scope hereof). The distal end 258 includes traditional threading adapted for secure attachment along the spinal column of an individual. According to exemplary embodiments of the present disclosure and with further reference to FIG. 23, the proximal end 256 of pedicle screw 216 is provided with a collet 260 that is sized for receipt in a substantially cylindrical receiving aperture/channel 262a formed within ball/spherical element 236.

Figure 23:
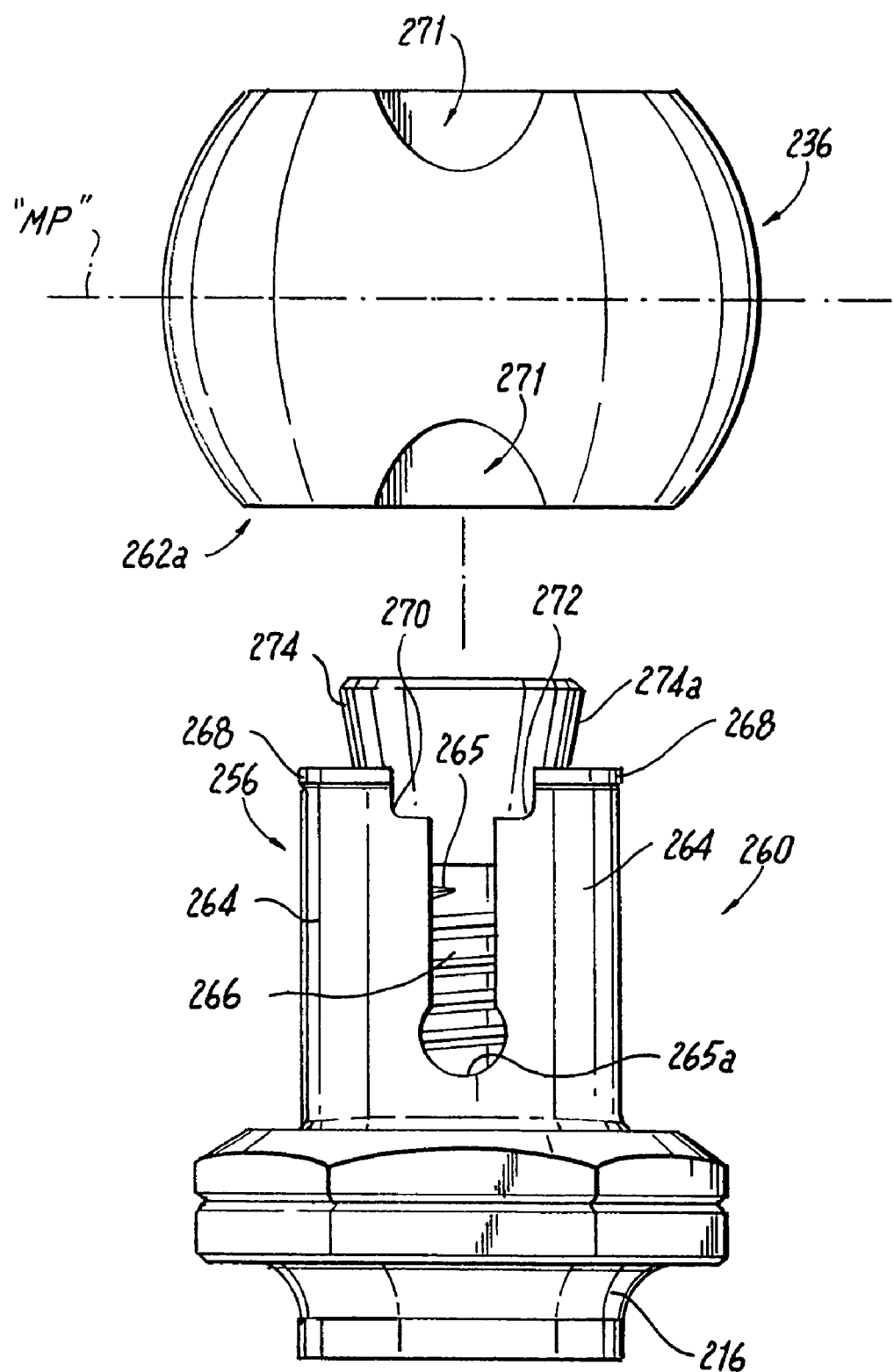
FIG. 23 is a side view of exemplary portions of a pedicle screw/ball joint subassembly (partially exploded) according to the present disclosure.

Collet 260 is fabricated and/or formed with an ability to expand and contract, e.g., under the control of medical practitioner(s) involved in using stabilizing system 211. Exemplary collet 260 includes a plurality of upstanding segments 264 that are arranged in a substantially arcuate manner around a central cavity 266, i.e., around the periphery of central cavity 266. Adjacent upstanding segments 264 are separated by a slot or channel 265. As shown in FIG. 23, slot 265 may define an enlarged, substantially circular region 265a at a base thereof. In exemplary embodiments of the present disclosure, circular region 265a further facilitates relative movement of adjacent upstanding segments 264.

With further reference to FIGS. 8 and 23, exemplary collet 260 defines three (3) upstanding segments 264 that are substantially identical in geometry/dimension, although alternative numbers, spacings and/or arrangements of upstanding segments 264 may be utilized and/or employed without departing from the spirit or scope of the present disclosure. As will be explained below in greater detail, the upstanding segments 264 are adapted for movement between: (i) an expanded (or outwardly deflected) state for locking collet 260 within a receiving channel 262a, 262b of a ball/spherical element 236, 238 and (ii) an unexpanded (or rest) state wherein the collet 260 may be selectively inserted or removed from a receiving channel 262a, 262b of a ball/spherical element 236, 238. Of note, the "expanded state" is generally not associated with a fixed or predetermined degree of expansion, but rather is generally defined by the level of expansion (i.e., outward deflection) required to achieve a desired frictional engagement between collet 260 and ball/spherical element 236, 238.

According to exemplary embodiments of the present disclosure, each of the receiving channels 262a, 262b of the respective balls/spherical elements 236, 238 is configured and dimensioned for receiving a collet 260 associated with a pedicle screw 216, 218 while in its unexpanded (or substantially unexpanded) state. Retention of the collet 260 may be further enhanced by the provision of a lip 268 at (or adjacent) the distal or upper end of upstanding segments 264 of collet 260. A lip 268 is generally formed on each upstanding segment 264, e.g., during the molding or machining of collet 260, and generally extends around the available perimeter of collet 260. Each of the receiving channels 262a, 262b generally includes first and second chamfered regions at opposite ends thereof. The chamfered regions facilitate alignment and connection of components of the disclosed stabilizing system, e.g., interaction between pedicle screws 216, 218 and balls/spherical elements 236, 238. To facilitate flexibility in use of the disclosed stabilizing system, balls/spherical elements 236, 238 are generally symmetric around or relative to a mid-plane (designated by phantom line "MP" in FIG. 23). Accordingly, the chamfered regions at either end of receiving channels 262a, 262b are substantially identical in geometry and dimension.

As noted above, lips 268 are formed on the outer walls of upstanding segments 264 and are advantageously configured and dimensioned to cooperate with the chamfered regions of receiving channels 262a, 262b. Thus, once collet 260 is extended through a receiving channel 262a, 262b, the lips 268 associated with upstanding segments 264 are generally positioned in a chamfered region associated with the receiving channel 262a, 262b. Frictional interaction between the lips 268 and the chamfered face of the receiving channel 262a, 262b generally helps to maintain relative positioning of the collet 260 and the receiving channel 262a, 262b, e.g., both before and after expansion of the collet 260 as described herein.

According to exemplary embodiments of the present disclosure, structural features and/or elements are provided on ball/spherical element 236, 238 and/or collet 260 to facilitate interaction with one or more tools, e.g., tools for securing a ball/spherical element 236, 238 relative to a pedicle screw 216, 218 and/or other components associated with stabilizing system 211. With reference to the exemplary system of FIGS. 8 and 23, alignment tabs or cut-outs 270, 272 are formed in upstanding segments 264 for tool interaction. The alignment tabs/cut-outs 270, 272 shown in FIG. 23 have a substantially L-shaped geometry, although alternative geometries may be employed to accommodate specific tool designs and/or tool interactions. In the exemplary embodiment of FIGS. 8 and 23, a tool (not pictured) may advantageously interact with adjacent alignment tabs/cut-outs 270, 272, e.g., through arcuately arranged gripping extensions that are spaced, configured and dimensioned to engage/cooperate with adjacent alignment tabs/cut-outs. As noted above, balls/spherical elements 236, 238 are generally symmetric relative to a mid-plane ("MP") and the disclosed alignment tabs/cut-outs 270, 272 are typically formed at both ends of balls/spherical elements 236, 238. Indeed, the provision of alignment tabs/cut-outs 270, 272 on both ends of balls/spherical elements 236, 238 advantageously facilitates the mounting of a ball 236, 238 in either orientation without sacrificing functionality/interactivity, e.g., interaction with an ancillary tool or the like. According to exemplary embodiments of the present disclosure, complementary notches 271 may be formed in balls 236, 238 to facilitate tool interaction. Notches 271 are generally spaced around the periphery of ball 236, 238, and may be brought into alignment with cut-outs 270, 272, e.g., by rotational reorientation of ball 236, 238 relative to collet 260, by a tool (not shown) in connection with tool-related manipulation thereof. Also, there can be geometry and/or structure on the pedicle screw which is configured to interact with the cut-outs on the ball/spherical element to automatically orient and provide rotational stability to allow for counter torque, e.g., when fixing the ball/spherical element relative to the pedicle screw.

Expansion of the exemplary collet 260 associated with pedicle screw 216, 218 may be achieved by the insertion of a set screw 274 within the central aperture 266 defined within upstanding segments 264 of collet 260. In accordance with an exemplary embodiment, set screw 274 is secured within the central aperture 266 via mating threads formed along the inner surface of the central aperture 266 and the outer surface of the set screw 274. Set screw 274 generally includes an outwardly tapered portion 274a, e.g., at or adjacent the non-threaded end thereof, which is configured and dimensioned to engage upstanding segments 264 of collet 260 as screw 274 is threaded relative to pedicle screw 216, 218. Thus, as set screw 274 moves downwardly within the central aperture 266, the upstanding segments 264 are contacted by the outwardly tapered portion 274a of screw 274 and are forced/deflected outwardly. Outward deflection of upstanding segments 264 increases the effective diameter of the collet 260, increasing (or establishing) interference contact between the outer surface of collet 260 and the inner wall of receiving channel 262a, 262b. By further insertion of set screw 274, collet 260 may be brought into locking engagement with the receiving channel 262a, 262b of ball/spherical element 236, 238. As noted previously, lips 268 may be provided on the outer surface of upstanding segments 264 to, inter alia, enhance the "locking" forces imparted by collet 260.

Figure 24A:
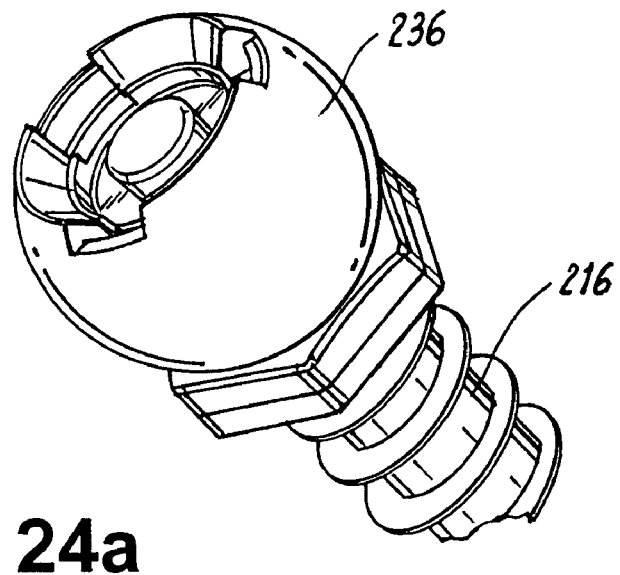
FIGS. 24a, 24b and 24c are views of an alternative collet-based mechanism according to the present disclosure.
Figure 24B:
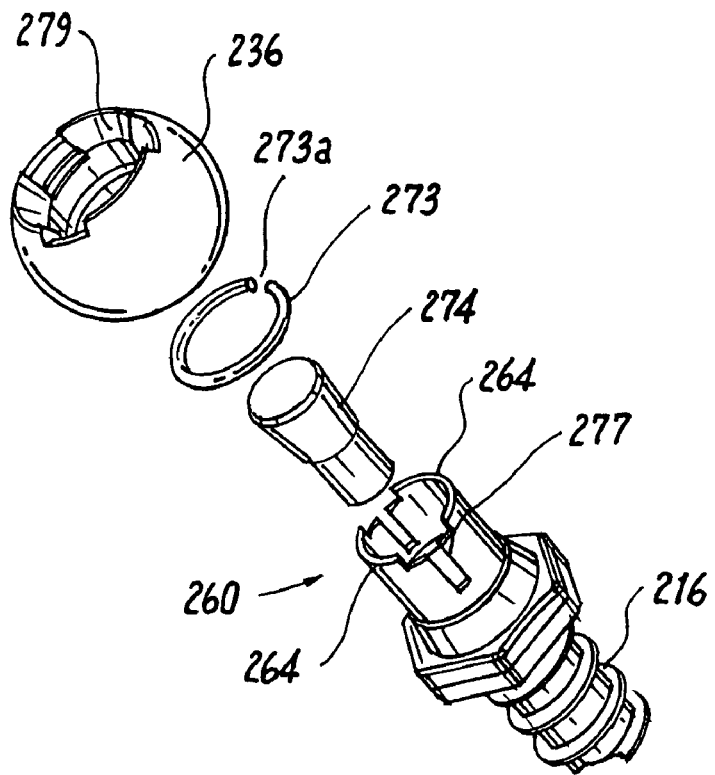
Figure 24C:
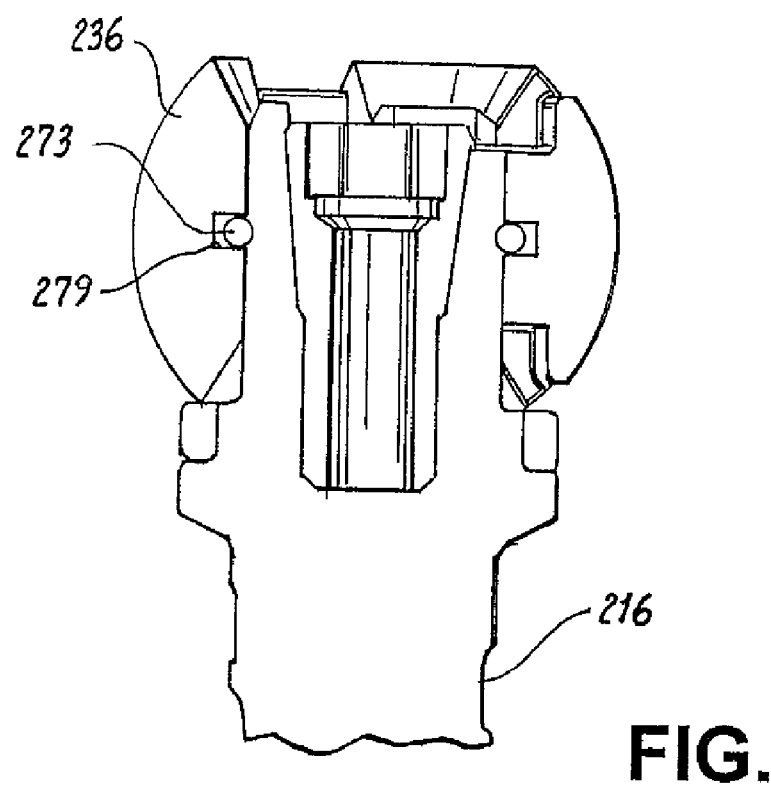

With reference to FIGS. 24a, 24b and 24c, an alternative collet-based system for securing or mounting a ball/spherical element relative to a pedicle screw according to the present disclosure is depicted. The collet-based system of FIGS. 24a-24c is similar to the system depicted in FIG. 23. However, in the system of FIGS. 24a-24c, an internal snap ring 273 is provided that is configured to cooperate with an external ring groove 277 formed in the outer wall of upstanding segments 264 and an internal ring groove 279 formed in ball/sphere 236. Snap ring 273 defines a partial circle, with opening 273a facilitating expansion of the diameter of snap ring 273. Typically, snap ring 273 is fabricated from an appropriate metallic material, e.g., titanium or stainless steel, that provides a desired degree of elasticity. The depths of external and internal ring grooves 277, 279, respectively, are generally selected to ensure seating of snap ring 273.

In use, snap ring 273 is typically positioned in the internal groove formed in the ball/spherical element and essentially "snaps" into place with the outer groove formed in the collet, i.e., when the components reach the desired alignment. This "snap" connection between the ball/spherical element and the collet/pedicle screw allows the clinician to take appropriate steps to more permanently secure the components relative to each other (e.g., locate and position appropriate tools) without risk that the components will become misaligned. Thus, the snap ring advantageously aligns with and partially nests within both ring grooves 277, 279, thereby providing a further engagement between ball/sphere 236. As set screw 274 is screwed into place, the upstanding segments 264 deflect outward, thereby providing a greater engagement between ball/sphere 236 and pedicle screw 216. In alternative embodiment hereof, the snap ring may be initially positioned on the outer surface of the collet (i.e., in the outer groove), in which case the snap ring "snaps" into the inner groove of the ball/spherical alignment when the desired alignment is achieved.

Of note, with a snap ring included in the disclosed assembly, the collet is no longer required to deform both inwardly and outwardly. The function of the lip on the collet may be replaced by the snap ring which separates the function of the temporary snap fit and final securement. Due to this separation of mechanical function imparted by snap ring 273, the depth of slots/channels 265 may be reduced in the exemplary embodiment of FIGS. 24a-24c relative to the embodiment of FIG. 23, without diminishing the effectiveness of secure interaction between the ball/spherical element and the collet. The potential for reducing the depth of slots/channels 265 arises because the slots/channels no longer need to allow deformation inward. Since only outward deflection of upstanding segments 264 is required to achieve the requisite securing force, the slot/channel depth may be reduced, thereby stiffening and strengthening the collet. The selection of an appropriate depth for slots/channels 265 is well within the skill of persons skilled in the art based on the present disclosure. By reducing the depth of slots/channels 265, greater strength may be imparted to collet 260.

Figure 25A:
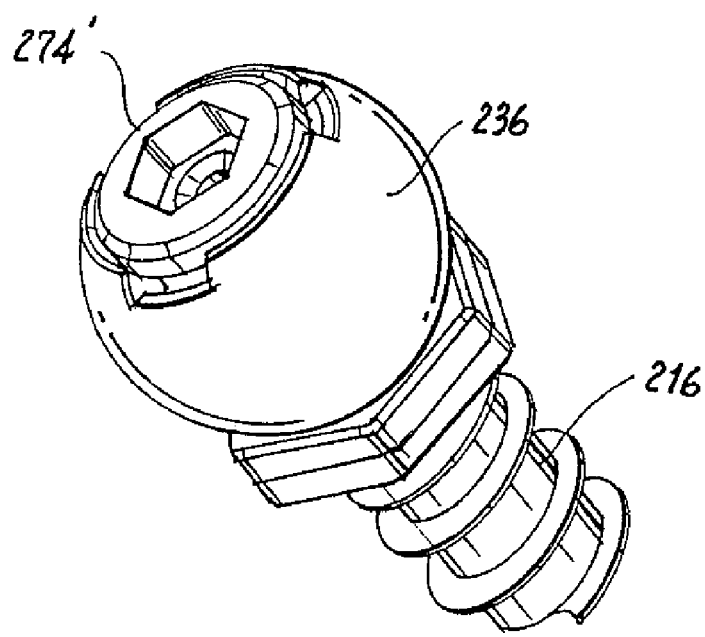
FIGS. 25a, 25b and 25c are views of a non-spreading collet-based mechanism according to the present disclosure.
Figure 25B:
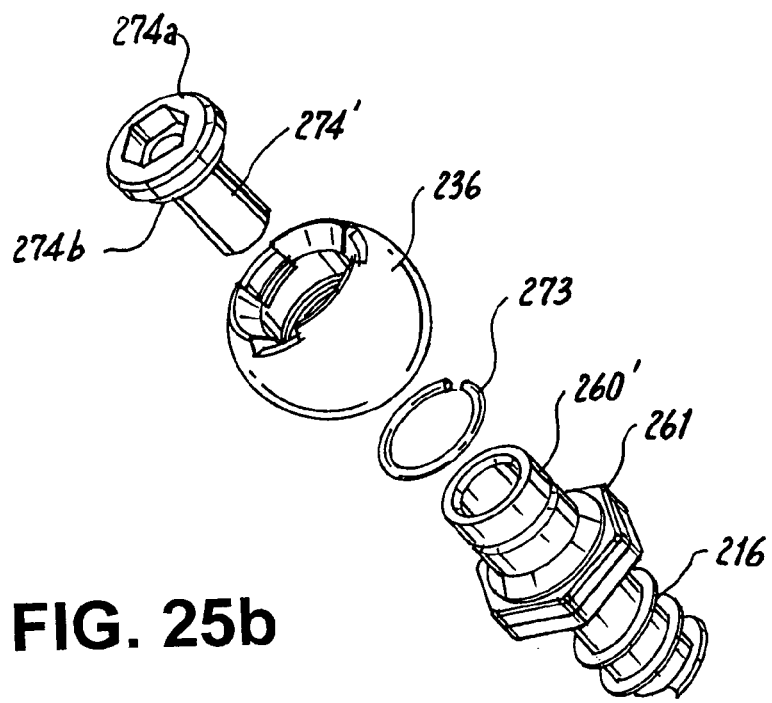
Figure 25C:
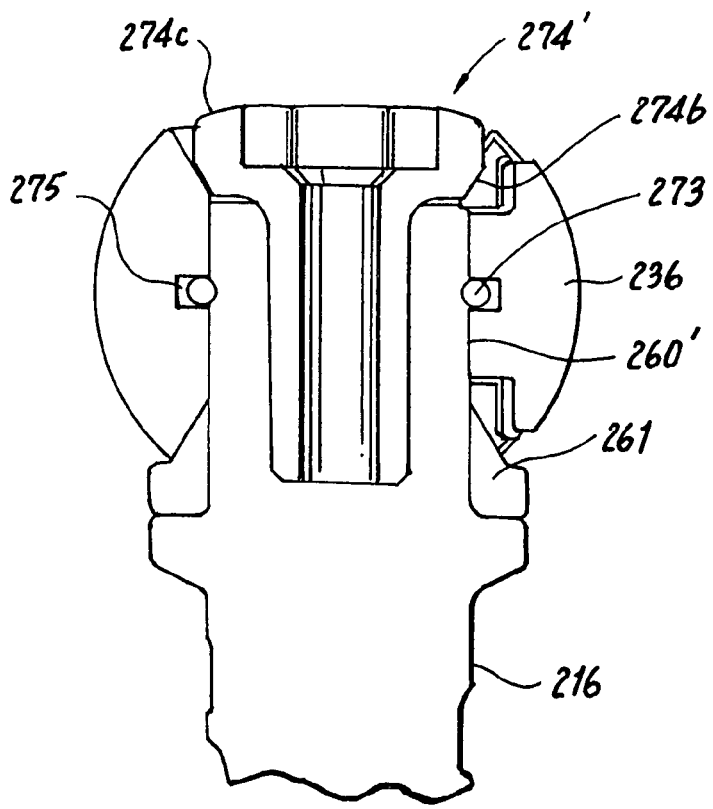

With reference to FIGS. 25a-25c, a further alternative mechanism is depicted wherein the collet is non-deflecting, i.e., the slots/channels from the preceding embodiments are eliminated. Thus, collet 260' defines a substantially cylindrical structure, rather than a plurality of upstanding, deflectable segments that are separated by slots/channels 265, as described with reference to the preceding embodiments. The cylindrical structure imparts additional strength to collet 260', relative to the previously described slotted embodiments. As with the embodiment of FIGS. 24a-24c, an internal snap ring 273 is provided and is adapted to nest within internal and external ring grooves 277, 279 in the manner described above. Interaction between snap ring 273 and ring grooves 277, 279 provides a securing force between collet 260' and ball/sphere 236.

With particular reference to the exploded view of FIG. 25b and the cross-sectional view of FIG. 25c, set screw 274' defines an enlarged head 274a that is dimensioned to cooperate with the chamfered opening to ball/sphere 236. A tapered, circumferential bearing surface 274b is defined on the lower portion of head 274a, which is adapted to engage ball/sphere 236 as set screw 274' is screwed into collet 260'. Cooperating screw threads are generally defined on the exterior of the downwardly extending portion of set screw 274' (e.g., 6-32 thread) and on the inner surface of collet 260'. Thus, as set screw 274' is advanced into collet 260', bearing surface 274b engages a cooperating chamfered surface on ball/sphere 236. At the same time, an angled, circumferential bearing surface 261 that is defined by (or associated with) pedicle screw 216 is brought into engagement with the symmetrically defined, chamfered surface at the opposite end of ball/sphere 236. Thus, the ball/sphere 236 is effectively captured between the enlarged head of set screw 274' and bearing surface 261 is positioned adjacent the base of collet 260'.

According to the alternative embodiment of FIGS. 25a-25c, the strength of the collet is increased through elimination of the slots/channels. In addition, the greater size of the enlarged head of set screw 274' permits a larger hexagonal (or other geometrically shaped) tool engagement feature relative to the previously described embodiments. Moreover, a "tissue-friendly" surface feature 274c may be defined on the upper surface of the enlarged head to shield tissue from the space within ball/spherical element 236. However, according to the embodiment of FIGS. 25a-25c, it is not possible to "preload" set screw 274' within the central aperture formed within pedicle screw (as described in greater detail below) because it is not possible to pass the ball/spherical element thereover.

Figure 26A:
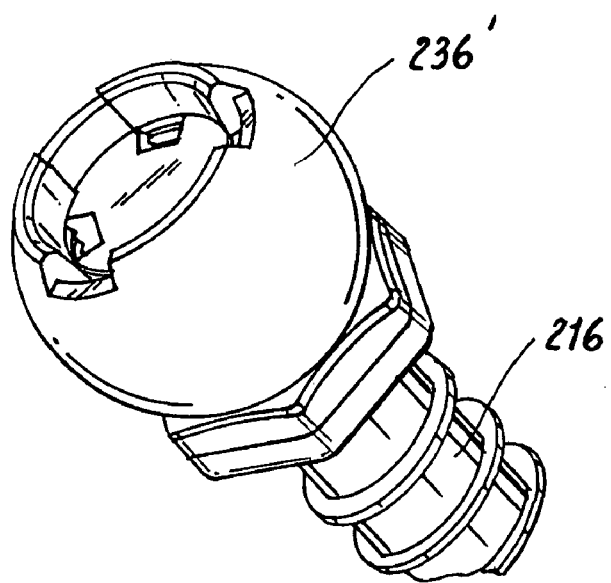
FIGS. 26a, 26b and 26c are views of a further alternative mechanism for mounting a ball/sphere relative to a pedicle screw according to the present disclosure.
Figure 26B:
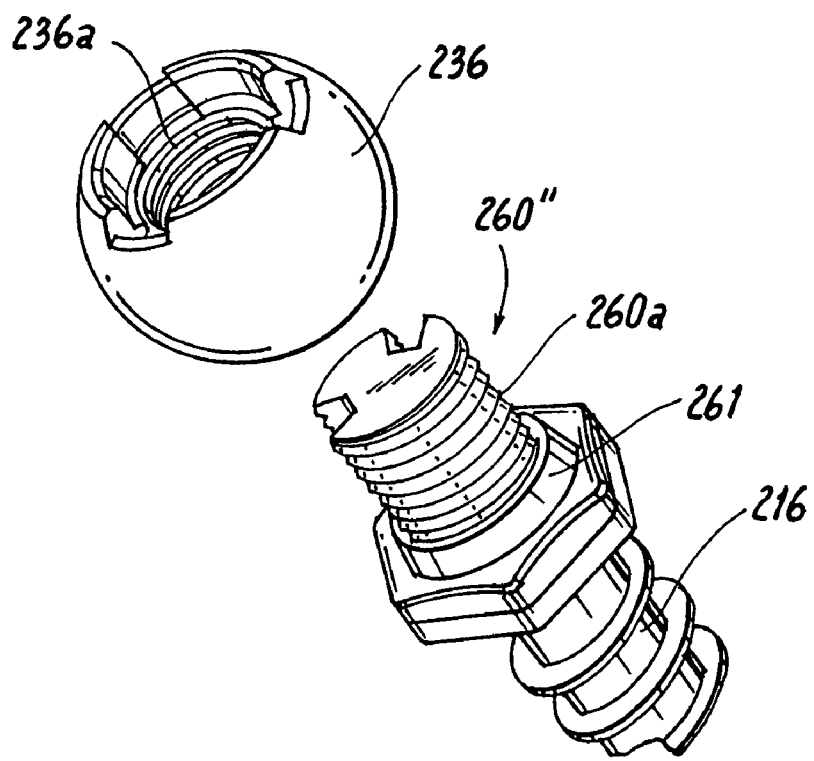
Figure 26C:
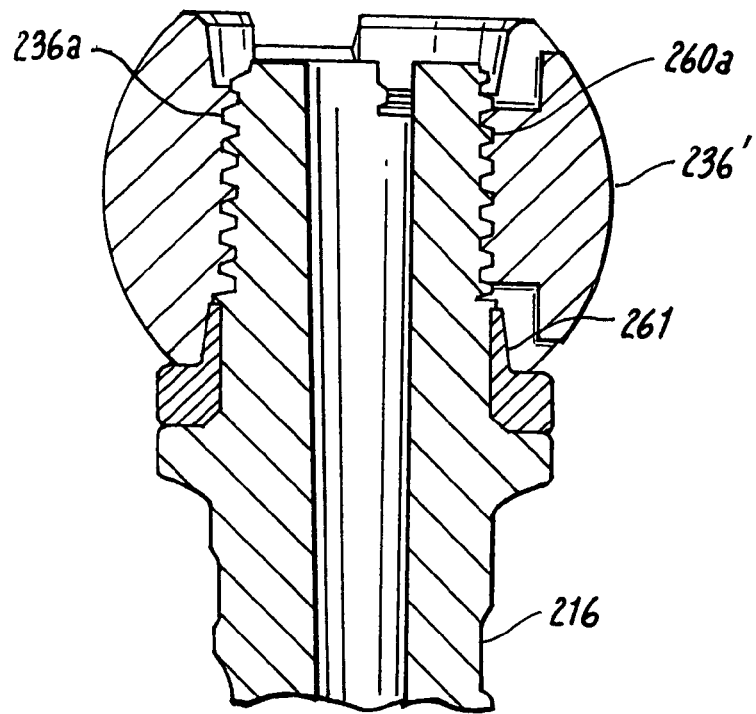

With reference to FIGS. 26a-26c, a further exemplary mechanism for securing or mounting a ball/sphere relative to a pedicle screw is depicted according to the present disclosure. As with the embodiment of FIGS. 25a-25c, a non-slotted collet is provided in association with pedicle screw. Also, as with the preceding embodiment, an angled, circumferential bearing surface 261 is positioned adjacent the base of the collet and is configured and dimensioned to engage an inner surface defined by the ball/sphere. Bearing surface 261 is defined by (or associated with) pedicle screw 216 and is positioned below the screw threads discussed below.

With particular reference to FIGS. 26b and 26c, ball/spherical element 236' defines a threaded inner surface 236a that is adapted to cooperate with an outwardly threaded surface 260a formed on collet 260". The cooperating threads obviate the need for, and utility of, the snap rings discussed with reference to prior embodiments. Of note, one or more features are generally formed at the openings of ball/sphere 236' to facilitate interaction with a tool (not pictured) for imparting rotational motion of ball/sphere 236' relative to pedicle screw 216. In like measure, one or more features are generally formed at (or near) the top of collet 260" to facilitate interaction with a counter-torque tool (not pictured) to ensure that rotation of ball/sphere 236 results in the desired tightening of ball/sphere 236' relative to collet 260". As ball/sphere 236' is tightened relative to collet 260", the bottom portion of the ball/sphere engages bearing surface 261, thereby providing further frictional engagement therebetween.

In use, the mounting mechanism of FIGS. 26a-26c obviates the need for a set screw (as described in previous embodiments) and utilizes a non-slotted collet, thereby imparting additional strength to the collet structure relative to previously disclosed slotted collets. Assembly of the ball/sphere and the pedicle screw requires thread alignment and appropriate tool interaction to effect the desired rotation of the ball/sphere relative to the collet/pedicle screw.

Figure 27:
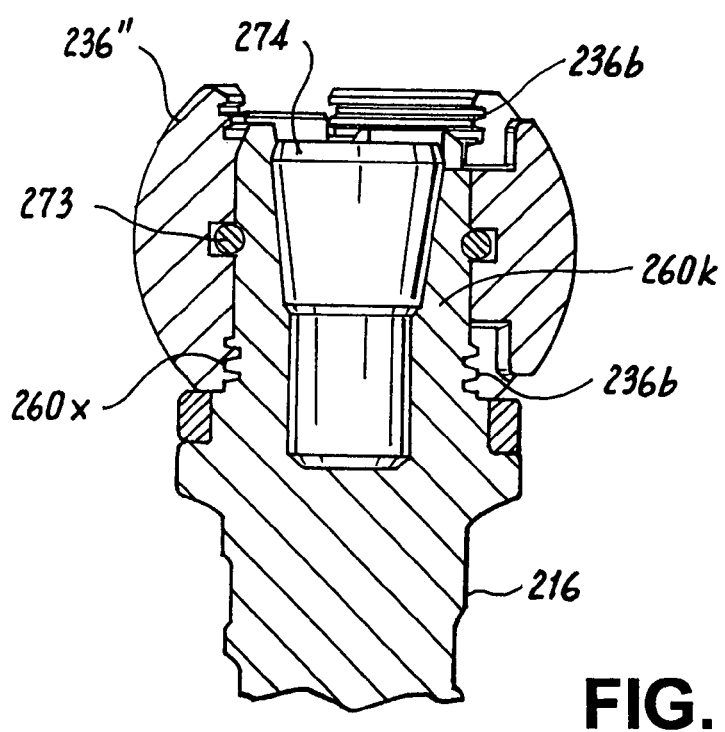
FIG. 27 is a cross-sectional side view an additional alternative mechanism for mounting a ball/sphere relative to a pedicle screw according to the present disclosure.

With reference to FIG. 27, a further alternative mounting mechanism is depicted wherein entry threads 236b on the ball/sphere 236" are configured to interact with cooperative threads 260x at (or near) the base of slotted collet 260k. A snap ring 273 is provided to supply further mounting security as the upstanding segments of the slotted collet 260k are deflected outward, i.e., when set screw 274 is advanced downward relative to pedicle screw 216. According to exemplary embodiments of the disclosed mechanism, the entry threads are "left-handed" threads, thereby minimizing the potential for disengagement thereof as set screw 274 is introduced. Indeed, as the set screw is advanced, the ball/sphere is urged into a locked position due to the oppositely oriented threading thereof. Alternatively, the set screw could be provided with left-handed threads, and the entry threads could be right-handed to achieve the same result. In use, the mounting mechanism of FIG. 27 provides enhanced mounting security between the ball/sphere and the collet/pedicle screw through the combined contributions of the deflectable upstanding segments of the collet (in response to set screw introduction), the inclusion of the snap ring, and the inclusion of entry threads on the ball/sphere.

According to exemplary embodiments of the present disclosure, set screw 274 is advantageously "preloaded" within central aperture 266, i.e., set screw 274 is partially threaded into central aperture 266 prior to commencing the clinical procedure. For purposes of the mounting mechanisms described above, only the design of FIGS. 25a-25c is not susceptible to a "preloaded" set screw (because of the enlarged head on set screw 274'). An interference may be provided on the surface of set screw 274 to maintain the set screw 274 in an initial "preloaded" position, e.g., during shipment and initial clinical positioning/introduction of the pedicle screw relative to a patient. An exemplary interference according to the present disclosure involves a deformation in the helical thread, e.g., at or near a distal end thereof. The deformation may be effected by striking the formed thread in one or more locations (e.g., two opposed locations) with a rigid surface. In an exemplary embodiment, a pair of deformations or "pings" are formed in the screw thread at or near the distal end of the set screw. It is further contemplated that a desired interference may be achieved by providing a limited region of "off-pitch" threading along the length of the screw thread. Alternative structures and/or mechanisms may be employed to achieve the desired interference (which is easily overcome by the clinician when he/she advances the set screw relative to the pedicle screw), as will be readily apparent to persons skilled in the art from the present disclosure.

By "preloading" the set screw as described herein, clinical use of the disclosed system is facilitated, e.g., potential difficulties associated with aligning set screw 274 with central aperture 266 during a clinical procedure and/or the potential for misplacing/dropping and/or cross-threading the set screw in connection with clinical activities are substantially eliminated. Of note, the length of set screw 274 and/or the relative dimensions and/or positioning of the outwardly tapered region of set screw 274 may be advantageously selected so as prevent or limit outward deflection of upstanding segments 264 in the "preloaded" configuration of set screw 274.

In general, tightening and/or locking of a ball/spherical element relative to a pedicle screw is thus undertaken according to exemplary embodiments of the present disclosure by threading a set screw into a central aperture positioned at or near the head of the pedicle screw. The set screw may be advantageously pre-loaded into the central aperture to facilitate clinical use thereof. Threading of the set screw into the central aperture causes an outward deflection of a series of upstanding segments associated with a collet mechanism associated with the pedicle screw. To facilitate movement of the set screw relative to the pedicle screw, it is generally desirable to impart a "counter-torque" force to the pedicle screw so as to prevent/limit rotational motion of the pedicle screw as the set screw is inserted or withdrawn relative to the central aperture. Tools for providing a desired counter-torque (and for inserting/withdrawing a set screw) are known. According to exemplary embodiments of the present disclosure, cut-cuts/alignment tabs may be formed or associated with the collet and cooperative notches may be formed or associated with the ball/spherical element to facilitate interaction with such tools, e.g., a tool for imparting a desired counter-torque force to the pedicle screw during set screw insertion/withdrawal.

Figure 29:
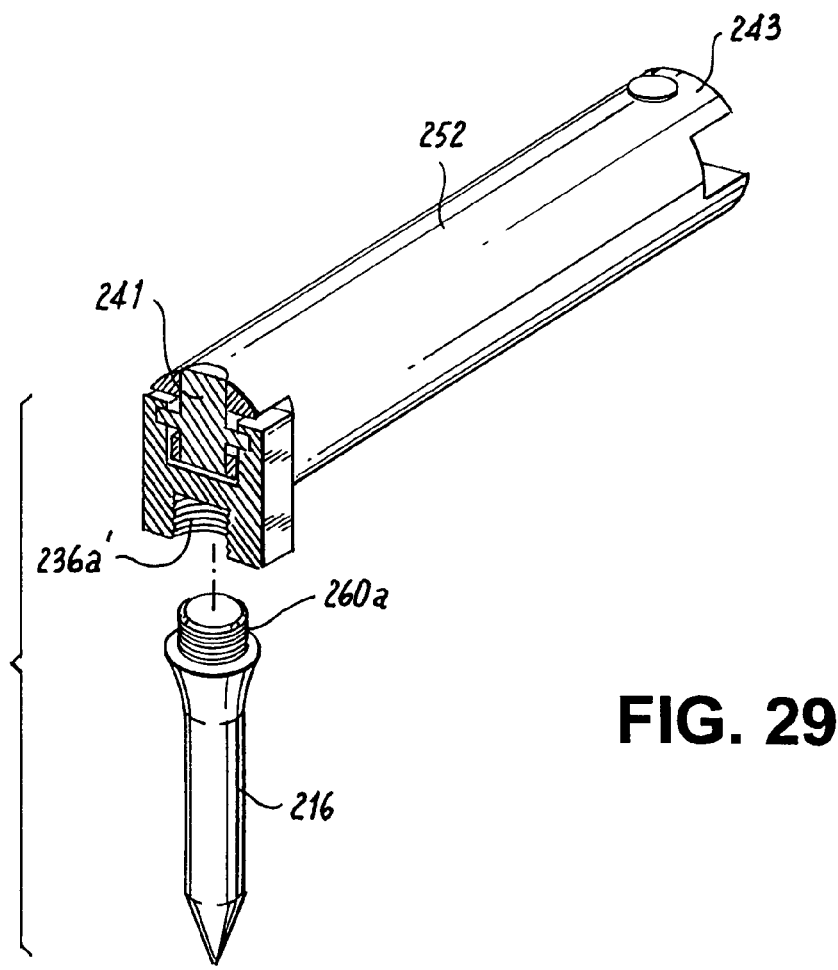
FIG. 29 is an exploded view of an alternative dynamic junction between a pedicle screw and accessory component(s) according to the present disclosure.

Although the present disclosure has described a series of exemplary embodiments wherein a ball/spherical element is mounted with respect to a pedicle screw and cooperates with a socket member to support motion relative to the pedicle screw (i.e., act as a motion interface element) and provide an advantageous dynamic junction, it is to be understood that the present disclosure is not limited to dynamic junctions formed through interaction between a ball/spherical element and a socket member. For example, as shown in FIG. 29, a pedicle screw 216 having an outwardly threaded collet 260a may engage an inwardly threaded cavity 236a that is mounted or jointed to a first universal joint mechanism 241 which functions as a motion interface element. A rod 252 cooperates with first universal joint mechanism 241 at a first end thereof and a second universal joint mechanism 243 at an opposite end thereof. The design and operation of universal joint mechanisms are well known to persons skilled in the art and implementation thereof in connection with pedicle screw mounting structures of the type disclosed herein provide advantageous alternative dynamic junctions for use in stabilization systems/applications. Alternative dynamic junction assemblies may also be employed without departing from the spirit or scope of the present disclosure, as will be readily apparent to persons skilled in the art from the detailed description provided herein.

As those skilled in the art will certainly appreciate, efficient and reliable alignment of ball/spherical element 236, 238 relative to collet 260 and within socket 232, 234 is desirable. In accordance with exemplary embodiments of the present disclosure and with reference to FIGS. 12 and 14, alignment activities are facilitated by providing clinicians with an advantageous guidewire system 275. Exemplary guidewire system 275 includes a guidewire 276 and a tapered guide member 278 that defines an outwardly tapered guiding surface (e.g., a conical surface) that is shaped and dimensioned to facilitate positioning of a ball relative to a pedicle screw and/or socket systems, as described herein. Guidewire 276 generally defines a proximal end 280 and a distal end 282 with a central portion 284 therebetween. In exemplary embodiments of the present disclosure, the proximal and distal ends 280, 282 of guidewire 276 are substantially similar to conventional guidewires that are used in conventional pedicle screw installations. However, the central section 284 is provided with an advantageous tapered guide member 278, as described herein.

Tapered guide 278 generally defines a sloped outer surface and a base 279 that is substantially planar. Base 279 is generally dimensioned to have a maximum diameter that is slightly smaller than that of the diameter of receiving channel 262a, 262b (as measured in the non-chamfered regions). Typically, the difference in diameter between base 279 of tapered guide 278 and the central channel of receiving channel 262a, 262b is about 0.001" to about 0.020", thereby facilitating alignment of a ball relative to a pedicle screw while simultaneously ensuring non-obstructed passage of the ball relative to the base of the tapered guide. In exemplary embodiments of the present disclosure, the distal end 282 of guidewire 276 extends within the pedicle screw 216, 218, e.g., to a position short of the distal end 258 of the pedicle screw 216, 218. The tapered guide member 278 is then advantageously positioned on guidewire 276 such that base 279 is adjacent the proximal end 256 of the pedicle screw, e.g., adjacent or in contact with collet 260.

In use, a pedicle screw may be introduced into a desired anatomical location. The disclosed guidewire system may then be advantageously employed to facilitate efficient and reliable positioning of a ball/sphere relative to the pedicle screw. The guidewire is generally fed into the pedicle screw such that the base of the disclosed tapered guide member is brought into close proximity and/or contact with the proximal end of the pedicle screw, e.g., the collet positioned at or near the head thereof. In percutaneous applications, however, the guidewire is generally positioned first, with the pedicle screw introduced to a desired anatomical location over the guidewire. A ball/spherical element (or alternative accessory structure) is then fed along the guidewire, i.e., the guidewire passes through the receiving channel of a ball/spherical element. The tapered guide member advantageously guides the ball into alignment with the proximal end of the pedicle screw, e.g., into alignment with a collet positioned at the head of the pedicle screw. The ball/sphere then passes over the base of the tapered guide member into position at the head of the pedicle screw, e.g., with an advantageous collet of the present disclosure positioned within the receiving channel of the ball.

It is contemplated that the tapered guide member of the present disclosure may be formed with various shapes designed to suit specific needs and/or applications. For example, the tapered guide member may be spirally shaped and provided with additional guides for ensuring that a ball has a proper orientation/registration when seated upon the collet. Such an embodiment might be used in minimally invasive procedures, e.g., to facilitate proper alignment with a set screw of an attachment member. In addition, the tapered guide member may advantageously include structures and/or features to facilitate rotational alignment or registration of a component, e.g., a component having at least one asymmetrical characteristic, relative to a pedicle screw. Thus, for example, a spiral may be provided on the tapered guide member that ensures proper alignment/registration with feature(s) on the pedicle screw.

In addition, a guiding cone or tapered guide member may be used according to the present disclosure to guide a screwdriver and/or a counter-torque device down the guidewire, e.g., to facilitate accessing of the set screw with limited or non-existent visualization. In an additional advantageous embodiment of the present disclosure, the guidewire system may facilitate tool alignment/guidance to an off-axis location, e.g., a laterally spaced attachment member and/or rod connector, based on a known lateral/off-axis direction and distance relative to the pedicle screw in which the guidewire is positioned. Thus, a guide member may be slid along the guidewire that effects a predetermined and advantageous off-axis positioning of, for example, a tool (e.g., a screw driver) relative to the guidewire.

Further, a tapered guide member according to the present disclosure may have a star-shaped or triangular profile. In addition, the tapered guide member may be provided as a separate component, i.e., for assembly with the guidewire at a desired point in time, e.g., during installation of a stabilization system according to the present disclosure. In implementations where the tapered guide member is provided as a distinct component relative to the guidewire (as opposed to a pre-assembled guidewire system), the tapered guide member is advantageously passed over the guidewire and positioned at a desired axial position during the stabilization system installation process. Indeed, it is further contemplated that the tapered guide member may be formed and used separately from a guidewire, e.g., by placing the tapered guide member in juxtaposition with the proximal end of a pedicle screw, e.g., by mounting a tapered guide member relative to a collet that is associated with a pedicle screw.

With further reference to the biasing structures of exemplary stabilizing member 210, a piston assembly 286 is provided that includes concentric springs 212, 214. The concentric springs take the form of an inner first spring 212 and an outer second spring 214. As will be described below in greater detail, the piston assembly 286 further includes a spring cap 288 and a spring cap rod 252 which translate and/or transmit forces between piston assembly 286 and pedicle screws 216, 218. Inasmuch as pedicle screws 216, 218 are substantially integral with spinal structures of a patient, the structural arrangement described herein effectively translates and/or transmits forces to and from a patient's spine.

The inner first spring 212 generally defines a first end 290 and a second end 292. As mentioned above, in exemplary embodiments of the present disclosure, first spring 212 is rigidly secured to first attachment member 224. The second end 292 of the inner first spring 212 is rigidly secured to abutment surface 294 of spring cap rod 252. The outer second spring 214 also defines a first end 296 and a second end 298. In exemplary embodiments of the present disclosure, the first end 296 of the outer second spring 214 is rigidly secured to spring cap 288 and the second end 298 of outer second spring 214 is rigidly secured to abutment surface 294 of spring cap rod 252.

As discussed above, the respective first and second springs 212, 214 are coupled to one or more structures associated with the exemplary stabilizing member 210. According to exemplary embodiments hereof, one or both springs 212, 214 may be rigidly (i.e., fixedly) coupled with respect to one or more component(s) associated with stabilizing member 210. In accordance with a preferred embodiment of the present disclosure, the springs are welded to structures at one or both ends thereof, although those skilled in the art will appreciate that other coupling techniques (e.g., nesting and/or capturing techniques) may be used without departing from the spirit or scope of the present invention.

The springs 212, 214 are generally positioned within a sheath 300, e.g., a substantially cylindrical member, to prevent undesirable interaction or interference between the springs and anatomical structures in situ. Thus, sheath member 300 is advantageously substantially inert with respect to surrounding anatomical structures and fluids. In accordance with exemplary embodiments of the present disclosure, sheath 300 is fabricated (at least in part) of ePTFE (expanded polytetrafluoroethylene), UHMWPE (Ultra-High Molecular Weight Polyethylene), polycarbonate-urethane composite materials (e.g., copolymers and/or blends thereof), or combinations thereof, although those skilled in the art will appreciate that other materials may be used without departing from the spirit or scope of the present invention. Sheath 300 is generally fabricated from a material with sufficient elasticity to accommodate axial elongation/contraction of stabilizing member 110, although structural arrangements to accommodate such axial motion, e.g., a bellows-like structure, may also be employed. It is contemplated that sheath 300 may include a surface treatment, e.g., a drug and/or medicinal agent, to facilitate or promote desired clinical results.

Abutment surface 294 of spring cap rod 252 is generally secured with respect to sheath 300 at a first end thereof, and spring cap 288 is generally secured with respect to sheath 300 at an opposite end thereof. Washers or C-clamps 302 are generally positioned at the junction between sheath 300 and the end member (i.e., spring cap 288 and abutment surface 294) to facilitate interaction therebetween. In an exemplary embodiment of the present disclosure, spring cap 288 is further rigidly secured with respect to body member 240 of first attachment member 224.

Figure 9:
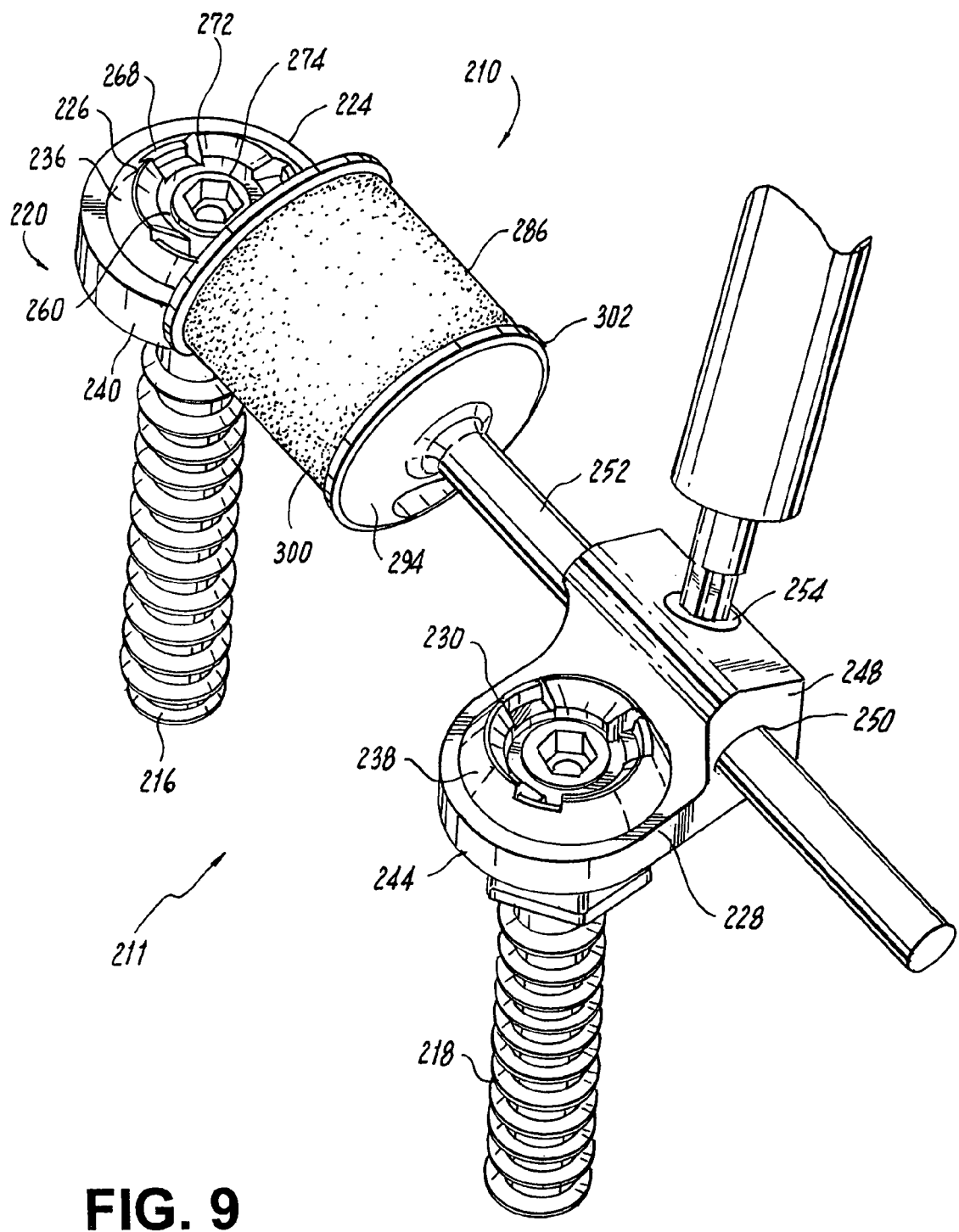
FIG. 9 is a perspective view of the exemplary dynamic spine stabilization system shown in FIG. 8.
Figure 17:
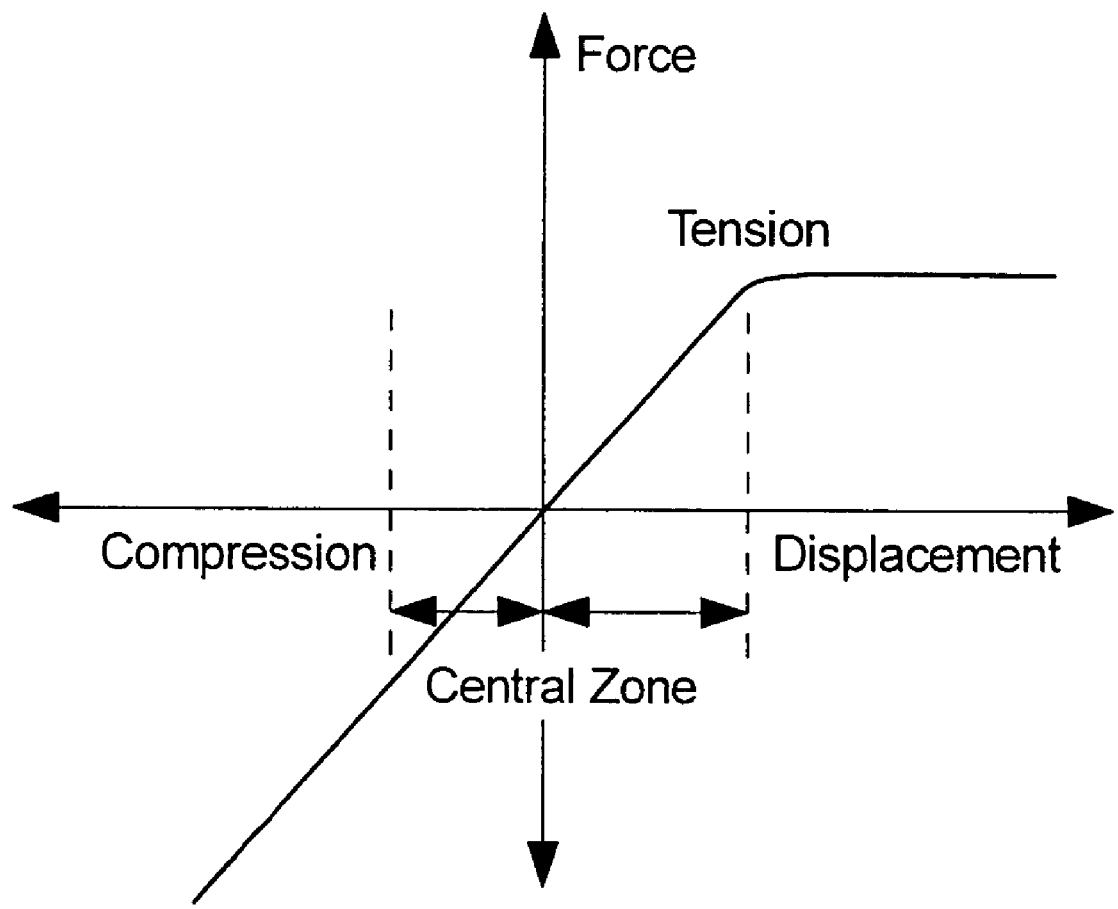
FIG. 17 is an illustrative Force-Displacement curve for an exemplary dynamic spine stabilization system according to the present disclosure.
Figure 18:
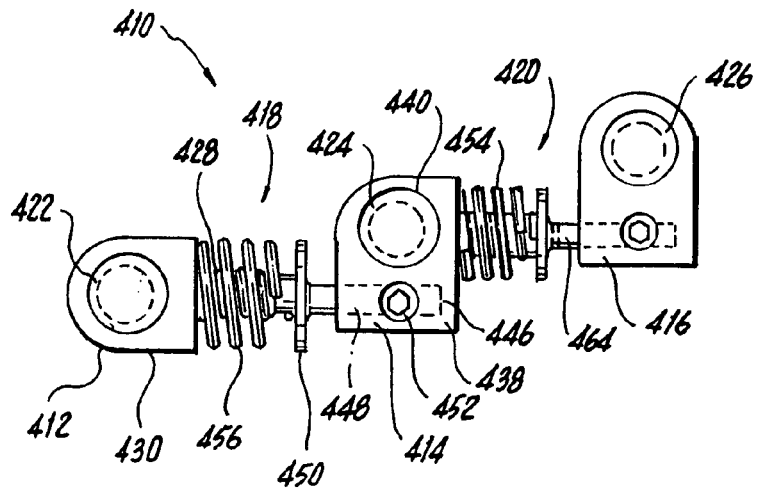
FIG. 18 is a schematic top view of an exemplary multiple level, dynamic spine stabilization system in accordance with an implementation of the present disclosure.

As shown in FIGS. 8 and 9, first and second springs 212, 214, spring cap 288 and spring cap rod 252 generally couple piston assembly 286 to pedicle screws 216, 218 in a manner providing a desirable and advantageous force profile, despite the limited anatomical space available in spine applications. For example, when the spine moves in extension, pedicle screws 216, 218 encounter forces that bias the pedicle screws toward each other. The forces experienced by pedicle screws 216, 218 are translated to forces on first and second attachment members 224, 228, which similarly are biased to move toward each other. The foregoing forces (that originate from spinal activity) generate a compressive force on stabilizing member 210. In response to the compressive force experienced by stabilizing member 210, a counterforce is generated within stabilizing member 210 through the spring force generated as spring cap rod 252 pushes and compresses outer second spring 214 between spring cap 288 and abutment surface 294 of spring cap rod 252. An additional counterforce is generated by stabilizing member 210 as spring cap rod 252 pushes and compresses the inner first spring 212 between the body 240 of the first attachment member 224 and the abutment surface 294 of the spring cap rod 252. As shown in FIG. 17, the combined spring forces of first spring 212 and second spring 214 creates a substantially uniform force profile in response to spine movement in tension, while extension generates compression across the spring member(s).

When the spine moves in flexion, pedicle screws 216, 218 are subject to forces that bias the pedicle screws away from each other. The forces experienced by pedicle screws 216, 218 as the spine moves in flexion are translated to first and second attachment members 224, 228, which similarly experience a force that biases such components of stabilizing system 211 away from each other. A counterforce is generated by stabilizing member 210 in response to flexion motion of the spine. The counterforce is generated in part as a result of the spring force generated when the spring cap rod 252 pulls upon and extends outer second spring 214 between the spring cap 288 and abutment surface 294 of spring cap rod 252. An additional counterforce is generated in response to flexion movement of the spine as spring cap rod 252 allows extension of the inner first spring 212 between the body 240 of first attachment member 224 and abutment surface 294 of spring cap rod 252. As the force profile of FIG. 17 shows, the operation of springs 212, 214 within stabilizing member 210 creates a force profile that advantageously decreases in intensity as overall spinal displacement increases/continues. At a certain point the inner spring reaches its free length and the resistance to motion is only in response to the increased elongation of the outer spring.

Referring to FIGS. 8 and 13-16, and in accordance with an exemplary embodiment of the present disclosure, stabilizer system 211 is generally installed in the following manner. Pedicle screws 216, 218 are positioned within the vertebrae using traditional techniques. The use of fluoroscopy for guidance of the pedicle screws is generally employed and strongly recommended. The pedicle screws 216, 218 are typically placed lateral to the facets in order to ensure that there is no interference between a facet and the implanted system. The pedicle is first opened with a high-speed burr or an awl. Thereafter, a stabilizer pedicle probe may be used to create a channel for pedicle screws 216, 218. The pedicles screws 216, 218 are generally self-tapping and therefore tapping of the pedicle screw channel typically is not required. The integrity of the pedicle channel wall is then typically checked and an appropriately sized pedicle screw 216, 218 is installed by attaching the screw to a screw driver and introducing the screw lateral to the facets. The pedicle screw 216, 218 is generally advanced until the head of the screw is in contact with the pedicle. Typically, placement of the pedicle screw 216, 218 as low as possible is very important, especially in the L5 and S1 pedicles. The placement of the pedicle screws 216, 218 is then generally checked with fluoroscopy, X-ray and/or other surgical navigation/viewing technique.

Once the pedicle screws 216, 218 are properly installed, the distance between the pedicle screws 216, 218 is generally measured and rod 252 of stabilizing member 210 may be cut to proper dimension, as appropriate. Alternatively, rods 252 of varying length may be provided to permit a clinician to select a rod of desired length. Still further, means for adjusting the length of a rod 252 may be employed, e.g., a telescoping rod with mechanism(s) for securing the rod at one or more desired lengths (e.g., detent mechanisms at fixed intervals, set screw systems for fixing the telescoping rod members relative to each other, or the like).

In installation procedures that employ a guidewire system to guide alignment and/or installation of system components, guidewire(s) 276 are positioned within one or both of the pedicle screws 216, 218. According to exemplary embodiments of the present disclosure, a tapered guide member 278 is advantageously positioned adjacent the top of collet 260. However, as noted previously, a tapered guide member may be directly associated with the pedicle screw and/or collet to facilitate alignment and/or installation of system components (e.g., in implementations that do not employ a guidewire).

An attachment member 224, 228 (which encompasses a ball/sphere 236) may be slid down along a guidewire 276 until a tapered guide 278 is reached. Once the attachment member 224, 228 reaches the tapered guide 278, a more exact guiding function is imparted to the attachment member. Indeed, tapered guide 278 advantageously functions to guide the ball-sphere 236 associated with attachment member 224, 228 into alignment with collet 260 such that it is positioned/aligned for efficient sliding passage thereover. Thus, tapered guide 278 brings the center line of the channel formed in ball/sphere 236 into substantial alignment with the center line of collet 260 so that collet 260 can readily slide through the ball/sphere 236. Depending on the mounting mechanism associated with interaction between the collet and the ball/sphere (see FIGS. 23-27), the aligned components are then mounted with respect to each other.

Thus, in the exemplary embodiment of FIGS. 8 and 15-16, set screw 274 is advantageously tightened within collet 260 to effect outward deflection of the upstanding segments, thereby locking/securing the ball 236, 238 in position relative to the collet/pedicle screw. Of note, in the exemplary embodiment of FIGS. 8 and 15-16, set screw 274 may be advantageously preloaded relative to collet 260, thereby facilitating the mounting process as described previously. For alternative mounting mechanisms described herein, appropriate steps may be undertaken to secure the ball/sphere relative to the collet, e.g., rotational motion of ball 236, 238 relative to the collet. Of note, ball 236, 238 is adapted for freely rotational motion relative to attachment member 224, 228, thereby facilitating rotational mounting of the ball, if desired.

At this stage of assembly/installation, a first ball is secured relative to a first collet/pedicle screw. However, according to the present disclosure, a dynamic junction is nonetheless established because the attachment member is free to move, e.g., rotate, relative to the ball. Indeed, a "race" is generally defined therebetween to facilitate relative movement between the ball and attachment member. As such, realignment and/or reorientation of the attachment member is possible so as to facilitate alignment with an adjacent pedicle screw, i.e., for assembly of a dynamic stabilization level. Of particular note, even after mounting of an attachment member relative to an adjacent pedicle screw, the dynamic junction remains operative at the initial pedicle screw described herein, thereby accommodating anatomical shifts that may arise after installation of the disclosed dynamic stabilization system.

With further reference to FIGS. 15-16, rod 252 is aligned with a receiving portion of rod connector 248 that is associated with second attachment member 228. As with the first attachment member discussed above, a dynamic junction is advantageously defined between socket 232 and ball/sphere 238 such that alignment between rod connector 248 and rod 252 is facilitated. Moreover, the functionality of the dynamic junction is unaffected by mounting of rod 252 relative to rod connector 248, i.e., rotational motion therebetween is not affected when a rod is secured/assembled according to the disclosed dynamic stabilization system. When rod 252 is properly aligned within rod connector 248, set screw 254 is tightened within transverse aperture 250 to lock rod 252 in position. The installation procedure is generally repeated on the opposite side of the vertebrae to complete a single level dynamic stabilization. Thus, at this stage in the assembly process, a dynamic stabilization is established for a single level, i.e., the level defined by the location of pedicle screws 216, 218 (and the associated counterparts on the opposite side of the vertebrae).

Figure 19:
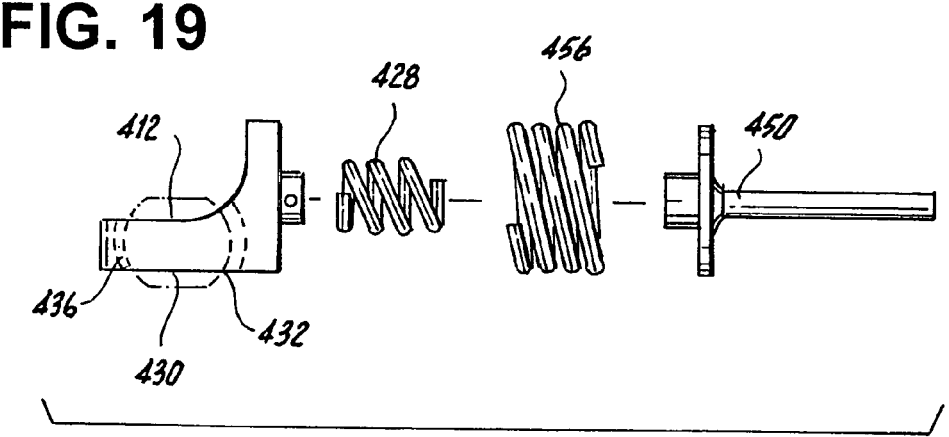
FIG. 19 is a schematic, exploded side view of a portion of the exemplary dynamic spine stabilization system of FIG. 18.
Figure 20:
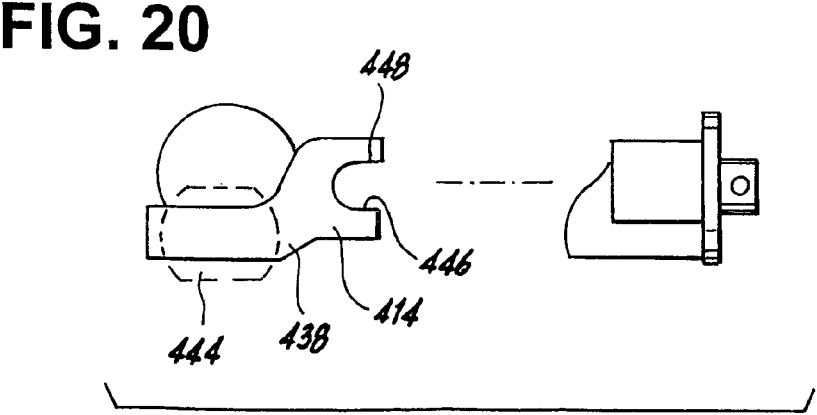
FIG. 20 is a schematic side view of an aspect of the exemplary dynamic spine stabilization system of FIG. 18.
Figure 21:
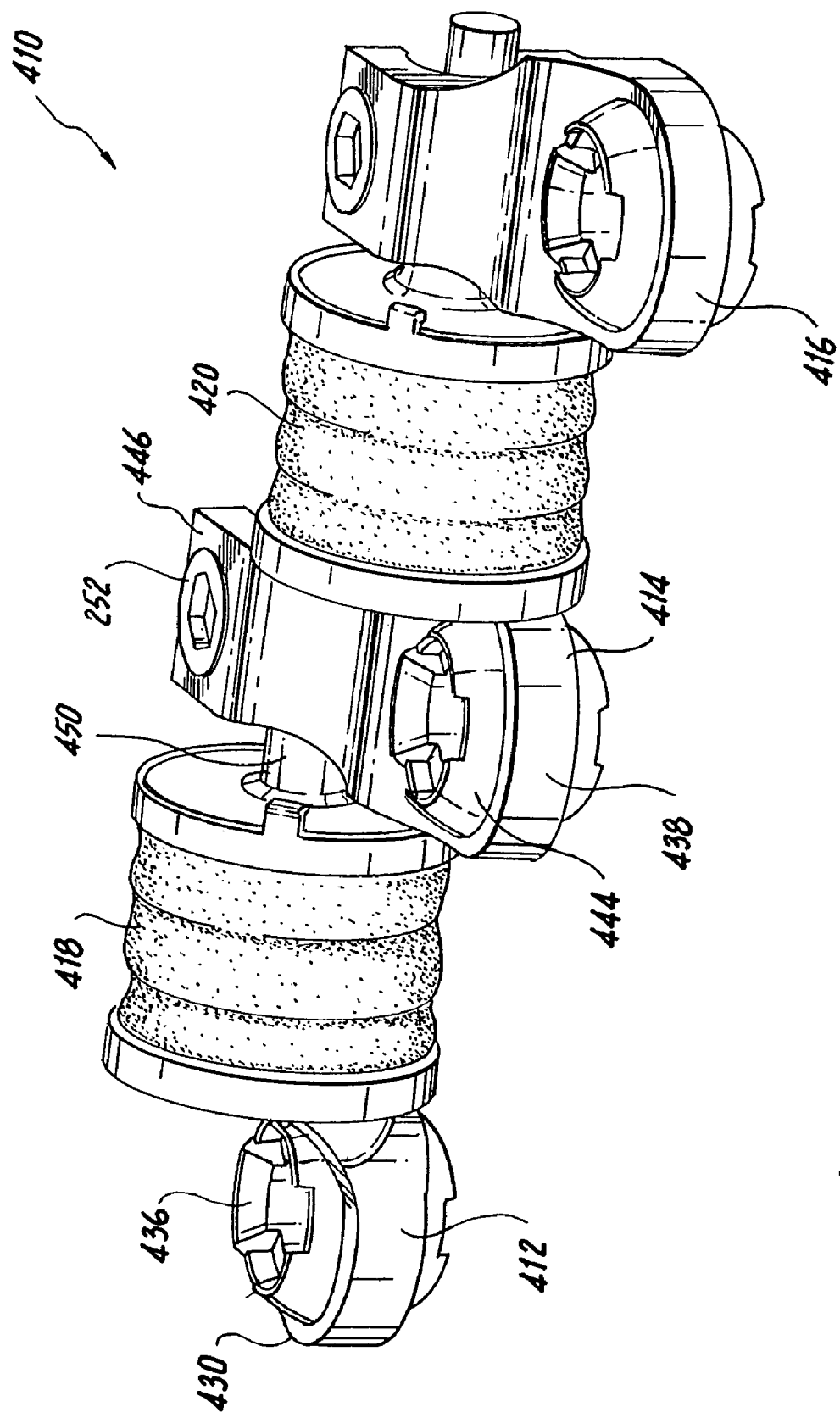
FIG. 21 is a perspective view of the exemplary multiple level, dynamic spine stabilization system of FIGS. 18 to 20.
Figure 22:
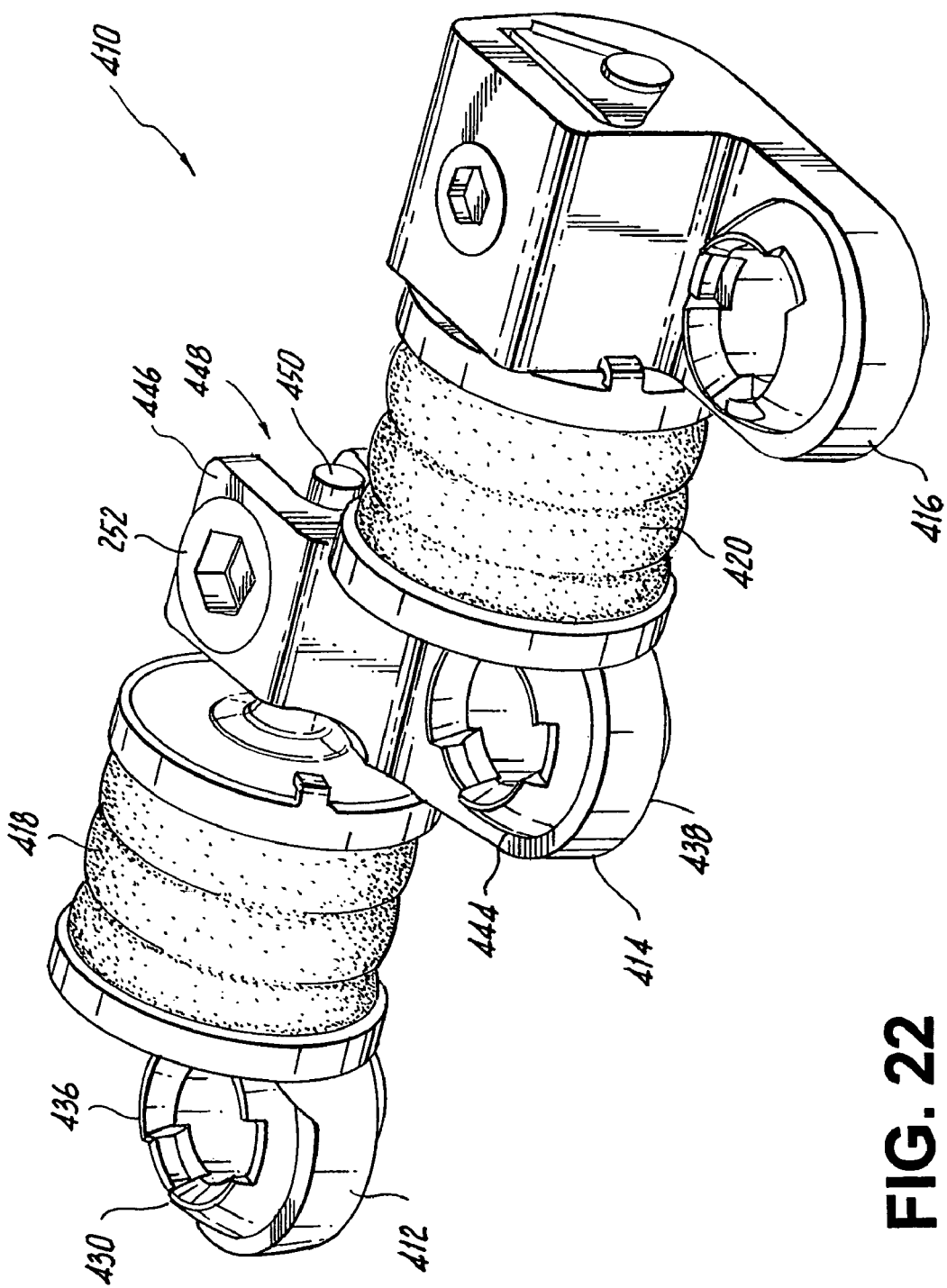
FIG. 22 is a further perspective view of the exemplary multiple level, dynamic spine stabilization system of FIG. 19.
Figure 30:
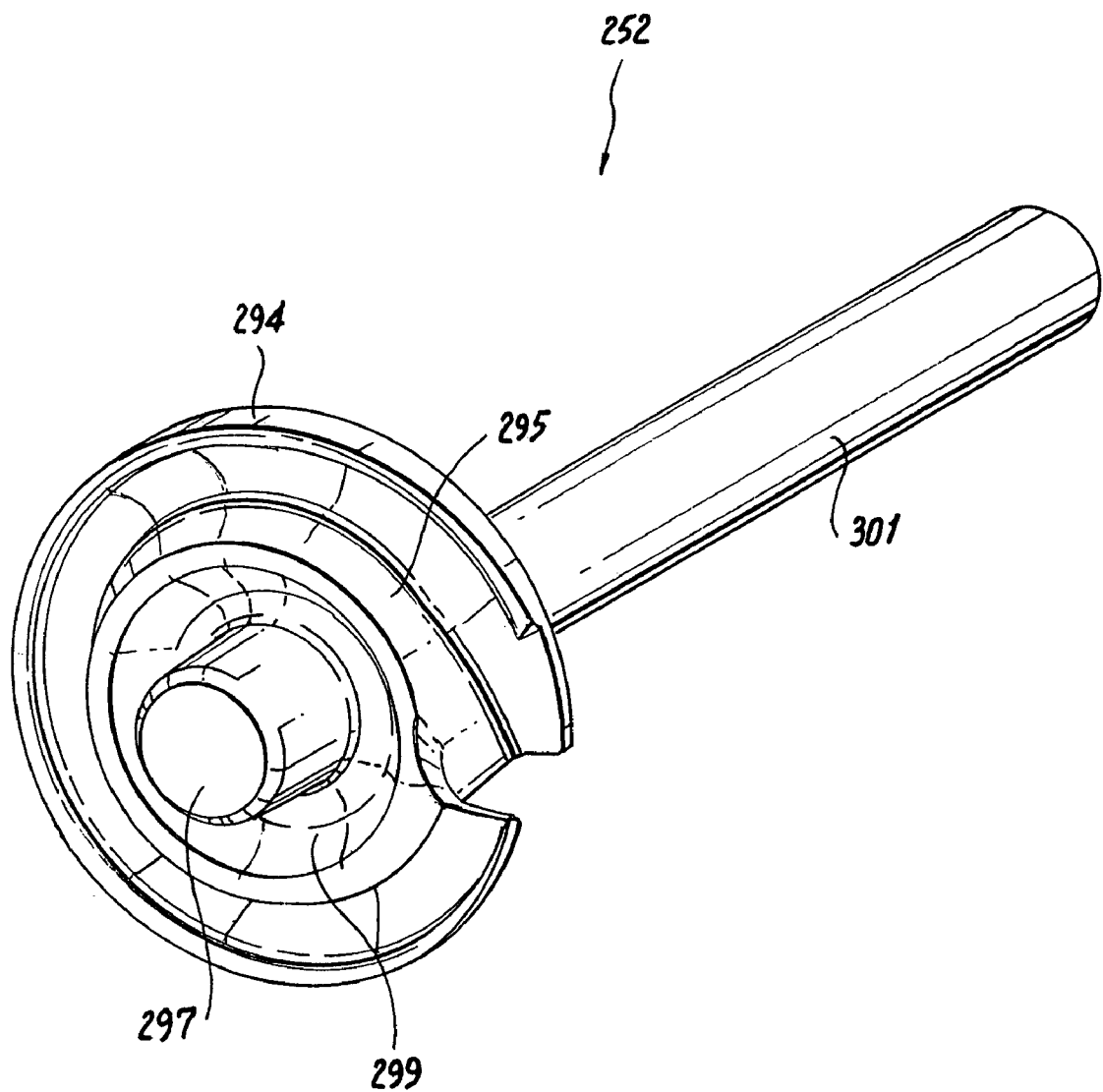
FIG. 30 is a perspective view of a spring cap rod according to an exemplary embodiment of the present disclosure.

With reference to FIGS. 28 and 30 (and corresponding structures in FIGS. 8 and 19), additional structural and assembly details associated with an exemplary embodiment of the disclosed dynamic stabilizing member are now provided. As noted above, first attachment member 224 includes spring cap 228. As shown in FIG. 28, spring cap 228 includes a helical groove 229 on the outer periphery of the flange-like structure of spring cap 228. The width and depth of groove 229 are generally sized so as to accommodate the wire gage of a helical outer spring (e.g., second spring 214 of FIG. 8 or second spring 456 of FIG. 19). In addition, a post 231 extends from the flange-like structure of spring cap 228. Post 231 is generally centrally located on the flange-like structure and extends away from socket 232. An annular cavity 233 may be formed around post 231. According to exemplary embodiments of the present disclosure and with reference to FIG. 30, abutment surface 294 of spring cap rod 252 includes a helical groove 295 (akin to helical groove 229), post 297 (akin to post 231) and annular cavity 299 (233). An elongated member (rod) 301 extends from abutment surface 294 in a direction opposite to post 297. The foregoing structures and features facilitate assembly and operation of exemplary dynamic stabilizing members according to the present disclosure.

More particularly, according to exemplary embodiments of the present disclosure, inner first spring 212 is initially positioned within second (outer) spring 214, and is then positioned around or on post 231 and the opposed post 297 that extends from abutment surface 294. According to exemplary assemblies of the present disclosure, inner first spring 212 advantageously extends into annular cavity 233 and the opposed cavity 299 formed in abutment surface 294. In this way, inner first spring 212 is effectively captured between spring cap 288 and spring cap rod 252, and essentially floats relative to the opposing posts 231, 297. Thereafter, second spring 214 is threaded into groove 229 formed in spring cap 288 (or the opposed groove 295 formed in abutment surface 294). Ultimately, second spring 214 is typically fixed with respect thereto, e.g., by welding, and may be trimmed so as to be flush relative to an outer edge of the flange-like structure to which it is mounted. The outer second spring 214 is then extended so as to be threaded onto the opposing groove, i.e., the groove associated with abutment surface 294 or spring cap 288, e.g., by rotating abutment surface 294 or spring cap 288 relative to second spring 214, as the case may be. Once threaded into the opposing groove, the second spring 214 is typically fixed with respect thereto, e.g., by welding, and may be trimmed to establish a flush edge.

Of note, outer second spring 214 is typically shorter than inner first spring 212. Thus, as abutment surface 294 and spring cap 288 are brought toward each other (to permit second spring 214 to be mounted on both), inner first spring 212 is placed in compression. The degree to which first spring 212 is compressed is generally dependent on the difference in length as between springs 212, 214. Thus, the preload compression of first spring 212 may be controlled and/or adjusted in part through selection of the relative lengths of springs 212, 214. In addition to the preload compression of inner spring 212, the mounting of outer spring 214 with respect to both spring cap 288 and abutment surface 294 places outer spring 214 in tension. The overall preload of a dynamic stabilizing member according to this exemplary embodiment corresponds to the equal and opposite forces experienced by springs 212, 214, i.e., the initial tension of outer spring 214 and the initial compression of inner spring 212.

According to exemplary embodiments of the present disclosure, inner spring 212 reaches its free length (i.e., non-compressed state) at or about the point at which a patient's movement exceeds the neutral zone. Beyond this point, inner spring 212 is free floating (on the opposed posts) and contributes no resistance to spinal movement. As described previously, the advantageous force profile supplied by the dynamic stabilization system of the present disclosure is achieved through utilization of inner and outer springs working synergistically. In particular, the force profiles for the springs are chosen to produce a reduction in the increase of mechanical resistance as the displacement moves beyond the neutral zone.

As briefly mentioned above, an axial spring configuration may be employed which generates the Force-Displacement curves shown with reference to FIG. 17, while allowing for a shorter distance between the first and second attachment members. As noted above, the Force-displacement curve is not exactly the same as that disclosed with reference to the embodiment of FIGS. 1 to 7. That is, the curve is substantially uniform during extension of the back and compression of the stabilizer, but the curve is substantially similar to that described with reference to FIGS. 3a and 3b when the back is in flexion and the stabilizer is elongated. The exemplary concentric spring design of the present disclosure allows a shorter distance between the first and second attachment members, eliminates the overhang on some previous embodiments, but this concentric spring orientation dictates that the extension curve be uniform or straight (i.e., no elbow). This profile characteristic results from the fact that both springs are loaded in extension, thus creating the exact same curve when both springs are loaded in the neutral zone, as compared to a situation wherein only one spring is loaded in flexion, i.e., while being elongated once outside the central zone of the device.

The advantageous dynamic stabilization systems disclosed herein may also be used in the stabilization of multiple level systems. Multiple level stabilization may be achieved through installation of a plurality stabilizing members coupled through a plurality of elongated members (e.g., rods) and a plurality of pedicle screws. For example and with reference to FIGS. 18 to 22, a multiple level, dynamic stabilization system 410 is schematically depicted. Multi-level stabilization system 410 may employ a variety of different attachment members 412, 414, 416. The different attachment member designs may be selected based on anatomical considerations, e.g., the spinal location for installation, and/or the position within the multi-level system. In other words, certain attachment member designs are better utilized at a first end or a second end, whereas other attachment member designs are suited for intermediate locations. While a specific combination of elements and/or components are disclosed in accordance with the exemplary multi-level stabilization system of FIGS. 18-22, those skilled in the art will readily understand from the present disclosure how the various attachment members and related structures/components may be employed to achieve dynamic stabilization at various spinal locations and/or in alternative deployment schemes.

Exemplary multi-level dynamic stabilization system 410 employs three distinct attachment members 412, 414, 416 dynamically linked by piston assemblies 418, 420 in the creation of a two level system. Of course, additional levels may be stabilized by extending the assembly with additional pedicle screws, collet/ball mounting mechanisms, dynamic stabilizing members, and elongated members/rods. The various attachment members are secured to the vertebrae through interaction with pedicle screws (not shown), as described above. Typically a dynamic junction is advantageously established between each pedicle screw (through cooperation with a ball/collet mechanism) and the attachment member mounted with respect thereto. The dynamic junction facilitates alignment with adjacent pedicle screw/attachment member subassemblies during installation/assembly of the multi-level dynamic stabilization system, and accommodates limited anatomical shifts/realignments post-installation.

With regard to dynamic stabilization between the first attachment member 412 and the second attachment member 414, the first attachment member 412 is structured for supporting inner first spring 428 and includes a body member 430 having an aperture 432 that extends therethrough. Body member 430 defines a socket 434 which is configured and dimensioned for receipt of ball 436, thereby establishing a first dynamic junction. According to the exemplary embodiment depicted herein, the inner first spring 428 extends from, and may be integrally formed with (or otherwise positioned with respect to), body member 430 of the first attachment member 412.

The second attachment member 414 similarly includes a body member 438 having an aperture 440 that extends therethrough. Body member 438 defines socket 442 which is configured and dimensioned for receipt of ball 444, thereby establishing a second dynamic junction. Second attachment member 414 further includes or defines a rod connector 446 with a transverse slot or channel 448 that extends therethrough. Transverse slot/channel 448 is configured and dimensioned to accommodate positioning and/or passage of stabilizer spring cap rod 450 therewithin. Spring cap rod 450 is generally secured within the transverse slot/channel 448 via a set screw 452 that extends between the external surface of rod connector 446 and the transverse slot/channel 448 formed by rod connector 446. As those skilled in the art will certainly appreciate, the transverse channel/slot may be structured in a variety of ways (e.g., as discussed above with reference to FIGS. 8-11). Second attachment member 414 is further associated with an inner first spring 454 that extends therefrom for interaction with third attachment member 416 (discussed below).

Piston assembly 418, which is positioned between first and second attachment members 412, 414, generally includes a pair of concentric springs. An inner first spring 428 and an outer second spring 456 are typically provided. As with the embodiment described above, inner first spring 428 and outer second spring 456 are secured with respect to an abutment surface 458 of spring cap rod 450 and body member 430 of first attachment member 412. Thus, first and second springs 428, 456 supply forces that act on (or with respect to) first and second attachment members 412, 414 during spinal movement, e.g., during extension and flexion of the spine. As is readily apparent from the discussion herein, the forces exerted on first and second attachment members 412, 414 are translated to forces on the associated pedicle screws, thereby stabilizing the vertebrae to which the pedicle screws are mounted.

Referring now to the relationship between second attachment member 414 and third attachment member 416, it is noted that the structural features of third attachment member 416 are substantially similar to those of second attachment member 414. However, in exemplary two-level stabilization systems disclosed herein, third attachment member 416 does not have an inner first spring 454 extending therefrom. Piston assembly 420 positioned between second and third attachment members 414, 416 is similar to the previously described piston assemblies. Generally, piston assembly 420 includes an inner first spring 454 that extends from second attachment member 414 and spring cap rod 464 extends from third attachment member 416.

As mentioned above, first, second and third attachment members 412, 414, 416 may have particular utility at particular anatomical locations. For example, it is contemplated that first attachment member 412 could be most useful at position S1 and below position L5, whereas second and third attachment members 414, 416 may be advantageously employed at L5 and above. Alternative implementations of the foregoing attachment members may be undertaken based on particular clinical needs and/or judgments.

Of note, single or multi-level dynamic spine stabilization systems/implementations according to the present disclosure permit one or more adjustments to be made (e.g., in situ and/or prior to clinical installation). For example, adjustments as to the magnitude and/or displacement-response characteristics of the forces applied by the stabilization system may be implemented, e.g., by substituting springs within one or more of the stabilizing members and/or adjusting the first/second housings, as described with reference to FIG. 8. The adjustments may be made prior to initiating a clinical procedure, e.g., based on an evaluation of a particular patient, or after a clinical procedure, e.g., based on post-surgical experiences of a patient.

According to further exemplary embodiments of the present disclosure, multi-level spinal stabilizations may be undertaken wherein the same or differing stabilization modalities may be employed at each of the individual levels. Thus, for example, a dynamic stabilizing member according to the present disclosure may be employed at a first stabilization level, a non-dynamic stabilizing member (e.g., a rigid structure/assembly such as a rigid rod or plate connection) at a second stabilization level, and a dynamic or non-dynamic stabilizing element at a third stabilization level. The advantageous flexibility and versatility of the disclosed systems/designs for mounting relative to a pedicle screw enhance the ability to vary the stabilization modalities from level-to-level according to the present disclosure. For example, upwardly extending collets disclosed herein readily accommodate cooperative mounting with respect to both dynamic and non-dynamic stabilizing members/elements. Indeed, it is contemplated according to the present disclosure that decisions as to stabilization modalities may be made at the time of surgery, e.g., based on clinical observations and/or limitations. Moreover, it is contemplated that dynamic and non-dynamic modalities may be interchanged at a point in time post-surgery. In such applications, a first stabilizing member (whether dynamic or non-dynamic) may be disengaged from a clinically installed stabilization system, and a second stabilizing member that offers a different modality may be installed in its place. Thus, systems according to the present disclosure encompass multi-level stabilizations that include at least one level that includes a dynamic stabilizing member and at least one level that includes a non-dynamic stabilizing element.

A kit may be advantageously provided that contains the components that may be necessary to perform clinical procedures according to the present disclosure, i.e., spine stabilization procedures. The kit contents are typically sterilized, as is known in the art, and may include appropriate labeling/indicia to facilitate use thereof. Typical kit contents include: (i) two or more attachment members (wherein one of the attachment members may include an extension member that incorporates a stabilizing member), (ii) two or more balls/spheres, and (iii) two or more pedicle screws. Alternative kits according to the present disclosure may include one or more of the following additional items: (iv) a variety or assortment of replacement springs for potential use in the dynamic stabilizing members of the present disclosure, (v) one or more tools for use in the dynamic stabilization procedures of the present disclosure (e.g., a screw driver, counter-torque device, measurement tools, tools for placement of the pedicle screws, etc.), (vi) one or more guidewires, (vii) one or more tapered guides or cones, and/or (viii) one or more set screws. The enclosures for the foregoing kits are typically configured and dimensioned to accommodate the foregoing components, and are fabricated from materials that accommodate sterilization, as are known in the art. A single kit may be broken into multiple enclosures, without departing from the spirit or scope of the present disclosure.

For exemplary embodiments of the present disclosure wherein springs are utilized in fabricating the disclosed dynamic stabilizing members, spring selection is generally guided by the need or desire to deliver a particular force profile or force profile curve, as described above. Generally, spring selection is governed by basic physical laws that predict the force produced by a particular spring design/material. However, the particularly advantageous dynamic spinal stabilization achieved according to the present disclosure (as described above and schematically depicted in FIGS. 3a, 3b and 17) require a recognition of the conditions and stimuli to be encountered in a spinal environment.

Figure 7A:
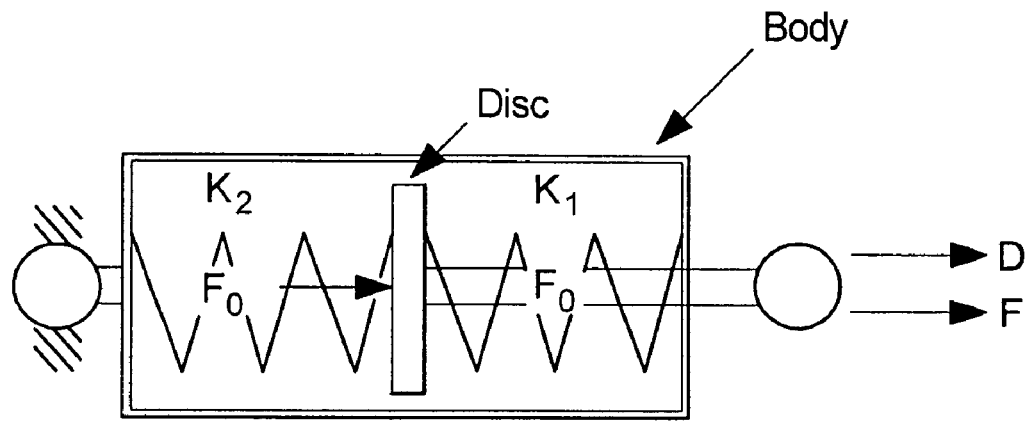
FIGS. 7a and 7b are, respectively, a free body diagram of an exemplary dynamic stabilizer according to the present disclosure and a diagram representing the central zone of such exemplary stabilizer.
Figure 7B:
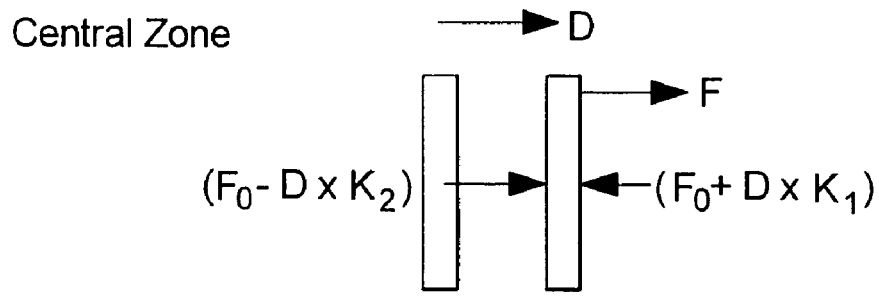

A first design criterion is the fact that the dynamic stabilizing member must function both in compression and tension. Second, the higher stiffness ($K_1+K_2$) provided by a disclosed dynamic stabilizing member in the central zone is generally achieved through the presence of a spring preload. Both springs are made to work together when the preload is present. As the dynamic stabilizing member is either tensioned or compressed, the responsive force increases in one spring and decreases in the other. When the decreasing force reaches a zero value, the spring corresponding to this force no longer contributes to the stabilizing functionality. An engineering analysis, including the diagrams shown in FIGS. 7a and 7b, is presented below. This analysis specifically relates to the exemplary embodiment disclosed in FIG. 5, although those skilled in the art will appreciate the way in which the analysis applies with equal force to all embodiments disclosed herein.

$F_0$ is the preload within the dynamic stabilizing member, introduced by shortening the body length of the housing as discussed above.

$K_1$ and $K_2$ are stiffness coefficients of the compression springs, active during tensioning and compression of the dynamic stabilizing member, respectively.

F and D are respectively the force and displacement of the disc of the dynamic stabilizing member with respect to the body of the dynamic stabilizing member.

The sum of forces must equal zero. Therefore, $$F+(F_0-D\times K_2)-(F_0+D\times K_1)=0, \text{ and}$$

$$F=D\times(K_1+K_2).$$

With regard to the central zone (CZ) width (see FIG. 3a): On Tension side $CZ_T$ is:

$$CZ_T=F_0/K_2.$$

On Compression side CZc is:

$$CZ_c=F_0/K_1.$$

While the foregoing analysis is useful in understanding the physical properties and forces associated with operation of the disclosed dynamic stabilizing member, the present disclosure is not limited to any theoretical or quantitative characterization of spring design or function. Rather, desired force profiles/force profile curves may be achieved through quantitative analysis, empirical study, or combinations thereof. In addition, as those skilled in the art will certainly appreciate, the concepts underlying the dynamic stabilization systems and associated components/assemblies may be applied to other clinical needs and/or medical/surgical procedures. As such, the disclosed devices, systems and methods may be utilized beyond spinal treatments without departing from the spirit or scope of the present invention.

Having described exemplary embodiments of the present disclosure, it is specifically noted that the present invention embodies a series of advantageous features and functions having particular utility in spinal stabilization devices/systems and associated methods, including the following:

Devices, systems and methods that provide a dynamic junction between at least one pedicle screw and at least one elongated member (or multiple elongated members), e.g., rod(s), that engage and/or otherwise cooperate with the pedicle screw. In exemplary embodiments of the present disclosure, the dynamic junction is provided through interaction between a collet/ball mechanism and a socket that is associated with an attachment member. The dynamic junction facilitates assembly of a spinal stabilization system and permits the pedicle screw/ elongated member to accommodate limited degrees of anatomical realignment/reorientation post-installation.

Devices, systems and methods that provide or incorporate ball assembly mechanisms that facilitate assembly/installation of a ball/sphere relative to a pedicle screw and provide advantageous functional attributes as part of a spinal stabilization system. Exemplary mechanisms include advantageous collet-based mechanisms (e.g., slotted and non-slotted collets), cooperatively threaded mechanisms (e.g., an externally threaded collet cooperating with an internally threaded ball/sphere), mechanisms that apply bearing forces against the ball/sphere (e.g., a circumferential bearing surface formed on a set screw having an enlarged head), and/or mechanisms that include a snap ring or analogous structure. The disclosed mechanisms permit reliable mounting of a ball/sphere relative to a pedicle screw.

Devices, systems and methods that provide dynamic spine stabilization systems/implementations over a single level and/or multiple levels, including single and multi-level systems that permit one or more adjustments to be made (e.g., in situ and/or prior to clinical installation), e.g., adjustments as to the magnitude and/or displacement-response characteristics of the forces applied by the stabilization system.

Devices, systems and methods that provide multi-level dynamic stabilization systems that include different stabilization modalities at different levels, e.g., at least one level including a dynamic stabilizing member and at least one level including a non-dynamic stabilizing member. According to exemplary embodiments of mixed multi-level stabilization systems, the dynamic and non-dynamic stabilizing elements are mounted with respect to common, i.e., identical, pedicle screws as disclosed herein.

Devices, systems and methods that provide or utilize advantageous installation accessories (e.g., cone structures) for facilitating placement and/or installation of spine stabilization system components, such accessories being particularly adapted for use with a conventional guidewires to facilitate alignment/positioning of system components relative to the pedicle screw.

Devices, systems and methods that provide or utilize dynamic spring stabilization components that include a cover and/or sheath structure that provides advantageous protection to inner force-imparting component(s) while exhibiting clinically acceptable interaction with surrounding anatomical fluids and/or structures, e.g., a cover and/or sheath structure that is fabricated (in whole or in part) from ePTFE, UHMWPE and/or alternative polymeric materials such as polycarbonate-polyurethane copolymers and/or blends.

Devices, systems and methods that provide advantageous dynamic spine stabilization connection systems that facilitate substantially rigid attachment of an elongated member (e.g., a rod) relative to the pedicle screw while simultaneously facilitating movement relative to adjacent structures (e.g., an adjacent pedicle screw) to permit easy and efficacious intra-operative system placement;

Devices, systems and methods that provide an advantageous "pre-load" arrangement for a securing structure (e.g., a set screw) that may be used in situ to mount a ball joint relative to a pedicle screw, thereby minimizing the potential for clinical difficulties associated with location and/or alignment of such securing structure(s).

Devices, systems and methods that embody or utilize advantageous kits that include an enclosure and necessary components for implementing dynamic spine stabilization in the manner described herein, such enclosure/components being supplied in a clinically acceptable form (e.g., sterilized for clinical use).

Although the present disclosure has been disclosed with reference to exemplary embodiments and implementations thereof, those skilled in the art will appreciate that the present disclosure is susceptible to various modifications, refinements and/or implementations without departing from the spirit or scope of the present invention. In fact, it is contemplated the disclosed connection structure may be employed in a variety of environments and clinical settings without departing from the spirit or scope of the present invention. Accordingly, while exemplary embodiments of the present disclosure have been shown and described, it will be understood that there is no intent to limit the invention by such disclosure, but rather, the present invention is intended to cover and encompass all modifications and alternate constructions falling within the spirit and scope hereof.

The invention claimed is:

1. A pedicle screw subassembly comprising:
(a) a threaded screw shaft;
(b) an upwardly extending collet that includes a plurality of downwardly extending slots, said slots defining a plurality of deflectable upstanding segments therebetween, wherein said upwardly extending collet defines a circumferential ring groove;
(c) a spherical element defining a substantially spherical outer surface and defining a cylindrical central passage that is configured and dimensioned such that said upwardly extending collet passes through said cylindrical central passage, said spherical element also defining an inner groove formed in said cylindrical central passage of said spherical element; wherein said substantially spherical outer surface is adapted to interact with an attachment member of a spine stabilizing system for dynamic motion therebetween; and
(d) a snap ring that defines a partial circle having a diameter and that includes an opening for facilitating expansion of the diameter of the partial circle, the snap ring being seated at least in part within both said inner groove of said spherical element and said circumferential ring groove of said upwardly extending collet, wherein said collet defines an internally threaded region that is adapted to receive a set screw.

2. A pedicle screw according to claim 1, wherein said collet includes three downwardly extending slots, and said three downwardly extending slots define three deflectable upstanding segments.

3. The pedicle screw subassembly according to claim 1, wherein said spherical element defines features to facilitate interaction with a counter-torque tool for imparting rotational motion of said spherical element relative to said pedicle screw.

4. A pedicle screw subassembly according to claim 1, wherein advancement of said set screw with respect to said internally threaded region causes outward deflection of said deflectable upstanding segments.

5. A pedicle screw subassembly according to claim 1, wherein said snap ring snaps into position at least partially in both said inner groove of said spherical element and said circumferential ring groove of said upwardly extending collet when said collet and said spherical element are in a predetermined alignment.

6. A pedicle screw subassembly according to claim 5, wherein said collet and said spherical element are secured in position when said snap ring snaps into position prior to said spherical element being locked with respect to said collet.

7. A pedicle screw according to claim 1, wherein said collet includes an outwardly threaded region in a base region thereof.

8. A pedicle screw subassembly according to claim 1, wherein said spherical element defines a non-dynamic stabilization element that defines a central passage that is configured and dimensioned such that said upwardly extending collet passes through said central passage and is secured with respect to said non-dynamic stabilization element.

9. A pedicle screw subassembly comprising:
   (a) a pedicle screw that includes a threaded screw shaft and an upwardly extending collet that includes a plurality of downwardly extending slots and a central, internally threaded region, wherein said slots define a plurality of deflectable upstanding segments therebetween and wherein said upwardly extending collet defines a circumferential ring groove;
   (b) a spherical element defining a substantially spherical outer surface and defining a cylindrical central passage that is configured and dimensioned such that said upwardly extending collet passes through said cylindrical central passage, said spherical element also defining an inner groove formed in said cylindrical central passage of said spherical element; wherein said substantially spherical outer surface is adapted to interact with an attachment member of a spine stabilizing system for dynamic motion therebetween;
   (c) a set screw that is configured and dimensioned to be advanced into said internally threaded region of said collet; and
   (d) a snap ring that defines a partial circle having a diameter and that includes an opening for facilitating expansion of the diameter of the partial circle, the snap ring being seated at least in part within both said inner groove of said spherical element and said circumferential ring groove of said upwardly extending collet.

10. A pedicle screw subassembly according to claim 9, wherein said spherical element is secured relative to said pedicle screw by advancing said set screw into said internally threaded region, thereby outwardly deflecting said deflectable upstanding segments into engagement with said spherical element.

11. A pedicle screw subassembly according to claim 9, wherein interaction between said collet, said spherical element and said snap ring functions to secure said spherical element relative to said pedicle screw prior to said spherical element being locked relative to said pedicle screw.

12. A pedicle screw subassembly according to claim 9, wherein said snap ring snaps into position at least partially in both said inner groove of said spherical element and said circumferential ring groove of said upwardly extending collet when said collet and said spherical element are in a predetermined alignment.

13. A pedicle screw subassembly according to claim 12, wherein said collet and said spherical element are secured in position when said snap ring snaps into position prior to said spherical element being locked with respect to said collet.

14. A pedicle screw subassembly according to claim 9, wherein said collet and said spherical element further comprise cooperative threads for threading engagement therebetween.

15. A pedicle screw subassembly according to claim 9, wherein said collet defines a bearing surface in a base region thereof, said bearing surface configured and dimensioned to apply a bearing force relative to said spherical element when said spherical element is secured relative to said pedicle screw.

16. A pedicle screw subassembly according to claim 9, wherein said central passage of said spherical element defines at least one chamfered entry region and wherein said deflectable upstanding segments define outwardly directed lips that are adapted to engage said chamfered entry region when said upstanding segments are outwardly deflected.

17. The pedicle screw subassembly according to claim 9, wherein said spherical element defines features to facilitate interaction with a counter-torque tool for imparting rotational motion of said spherical element relative to said pedicle screw.

* * * * *